US008143485B2

(12) United States Patent
Despeghel et al.

(10) Patent No.: US 8,143,485 B2
(45) Date of Patent: Mar. 27, 2012

(54) FAD-2 MUTANTS AND HIGH OLEIC PLANTS

(75) Inventors: Jean-Pierre Despeghel, Ingre (FR);
Kunsheng Wu, Ballwin, MO (US);
Nelly Guguin, Saclas (FR)

(73) Assignee: Monsanto S.A.S., Lyons (FR)

( * ) Notice: Subject to any disclaimer, the term of this patent is extended or adjusted under 35 U.S.C. 154(b) by 428 days.

(21) Appl. No.: 12/282,696

(22) PCT Filed: Mar. 21, 2007

(86) PCT No.: PCT/EP2007/052702
§ 371 (c)(1),
(2), (4) Date: Mar. 2, 2009

(87) PCT Pub. No.: WO2007/107590
PCT Pub. Date: Sep. 27, 2007

(65) Prior Publication Data
US 2009/0202703 A1 Aug. 13, 2009

(30) Foreign Application Priority Data
Mar. 21, 2006 (EP) .................................. 06290457

(51) Int. Cl.
*A01H 5/00* (2006.01)
*C12N 15/82* (2006.01)
*C07H 21/04* (2006.01)
*C12N 5/10* (2006.01)
(52) U.S. Cl. ....... 800/298; 800/281; 536/23.2; 435/419; 435/410
(58) Field of Classification Search ........................ None
See application file for complete search history.

(56) References Cited

U.S. PATENT DOCUMENTS

| | | | |
|---|---|---|---|
| 4,627,192 A | 12/1986 | Fick | |
| 5,338,471 A | 8/1994 | Lal | |
| 5,773,391 A | 6/1998 | Lawate et al. | |
| 5,965,755 A | 10/1999 | Sernyk et al. | |
| 6,010,545 A | 1/2000 | Davies et al. | |
| 6,312,623 B1 | 11/2001 | Oommen et al. | |
| 7,109,392 B1 | 9/2006 | Broglie et al. | |
| 2005/0079258 A1 | 4/2005 | Wester et al. | |
| 2005/0126071 A1 | 6/2005 | Krull et al. | |

FOREIGN PATENT DOCUMENTS

| | | |
|---|---|---|
| AT | 397966 B | 1/1993 |
| CA | 2180386 A1 | 1/1998 |
| EP | 0945514 A | 9/1999 |
| EP | 1541664 A1 | 6/2005 |
| EP | 1806398 A | 7/2007 |
| EP | 1862551 A | 12/2007 |
| GB | 642718 | 9/1950 |
| JP | 05039497 | 2/1993 |
| WO | 9115578 A1 | 10/1991 |
| WO | 9411516 A | 5/1994 |
| WO | 9721340 A1 | 6/1997 |
| WO | 9856239 A | 12/1998 |
| WO | 03085070 A2 | 10/2003 |
| WO | 03093403 A1 | 11/2003 |
| WO | 2004072259 A2 | 8/2004 |
| WO | 2006002683 A1 | 1/2006 |
| WO | 2006079567 A | 8/2006 |
| WO | 2006094138 A2 | 9/2006 |

OTHER PUBLICATIONS

Broun et al, Science 282:1315-1317, Nov. 13, 1998.*
Van de Loo et al, PNAS, USA 92: 6743-6747, Jul. 1995.*
Doerks et al, TIG 14(6): 248-250, Jun. 1998.*
Brenner et al, SE, TIG 15(4): 132-133, Apr. 1999.*
Bork et al, TIG 12(10):425-427, Oct. 1996.*
Fourgoux-Nicol et al, Plant Mol Biol 40: 857-872, 1999.*
Office action issued in U.S. Appl. No. 11/571,555, dated Jul. 10, 2009, 9 pages.
Anonymous, "Types of Oils," Internet Article Retrieved Apr. 26, 2005, URL: http://www.Iasc-Oils.Org/Types%20OF%20OILS.htm.
Bondioli, R, et al., "Biodiesel Stability Under Commercial Storage Conditions Over One Year," 2003, Eur. J. Lipid Sci Technol., 104:735-741.
Carre, P., et al., "Technological Performances of Low Linolenic/High Oleic Rapeseed Oils for Food and Non-Food Application," Proceedings The 12th Annual Rapeseed Congress, V, Sustainable Development in Cruciferous Oilseed Crops Production, Wuhan, China, Mar. 26-30, 2007, Science Press USA Inc., pp. 152-159.
Corbett, "Research in the Area of High Oleic Oils," 2002, Diversification of Canadian Oilseeds Part 1: Adding Value to the Oil, NRC-PBI Bulletin, 2002, Issue 1, 3 pages.
Friedrich, S., "A World Wide Review of the Commercial Production of Biodiesel," 2004, Institut Fur Technologie Und Nachhaltiges Produktmanagement, 164 pages.
Topfer, R., et al., "Modification of Plant Lipid Synthesis," 1995, Science, 268:681-686.
Brassica Breeding and Research, For Growers, University of Idaho Web Site: http://www.ag.uidaho.edu/brassica/forgrowers.htm, retrieved Jan. 23, 2008, 6 pages.
Database EMBL, EL598 Brassica Embryo Library (EL) Brassica Napus cDNA Clone EL598 Complete, mRNA sequence, 2005. Database Accession No. CN830902.
Setting National Fuel Quality Standards, Paper 6, National Standard for Biodiesel Discussion Paper prepared by Environment Australia, Mar. 2003, Department of the Environment and Heritage, Commonwealth of Australia, 119 pages.
Austrian Biofuels Institute, Report for the IEA, "Biodiesel—A Success Story: The Development of Biodiesel in Germany," Vienna, Austria, Jun. 2001, Update Feb. 2002, Total Pages 41.
International Search Report Issued in PCT/EP2004/011340, dated Jun. 27, 2005, 3 pages.
International Search Report and Written Opinion issued in PCT/EP2006/062746, dated Sep. 13, 2006, 13 pages.

(Continued)

Primary Examiner — Elizabeth McElwain
(74) Attorney, Agent, or Firm — Senniger Powers LLP

(57) ABSTRACT

The present invention relates to plants, seeds and products derived thereof, in particular to *Brassica* plants, seeds products derived thereof, that have mutant sequences conferring high oleic acid profile on the seed oil. More particularly, the invention relates to mutant delta-12 fatty acid desaturase sequences, also referred to herein as FAD2 sequences, —insuch-plants which confer high oleic acid profile on the seed oil.

16 Claims, 14 Drawing Sheets

OTHER PUBLICATIONS

International Search Report and Written Opinion issued in PCT/IB2006/003847, dated Jul. 26, 2007, 18 pages.

International Search Report and Written Opinion issued in PCT/IB2007/001540, dated Dec. 28, 2007, 18 pages.

Database EMBL, "Sequence 12 from Patent EP 1806398," Retrieved from EBI Accession No. EMBL: CS628394, Database Accession No. CS628394, Jul. 19, 2007.

European Search Report and Written Opinion issued in EP 07 29 0043, dated May 19, 2007, 6 pages.

International Search Report and Written Opinion issued in PCT/EP2008/050307, dated May 6, 2008, 20 pages.

Office action issued in U.S. Appl. No. 12/160,015, dated May 13, 2011, 15 pages.

* cited by examiner

FIG. 1A

| SEQ ID NO 1 | ATGGGTGCAGGTGGAAGAATGCAAGTGTCTCCTCCCTCCAAAAAGTCTGAAACCCGACAACATCAAGCGCGTACCCTGCGAGACACCGCCTTCA<br>CTGTCGGAGAACTCAAGAAAGCATTCGCACCGACTGTTTCAAACGCTGATCCGTCTCTTCTCCTCATCTGGGACATCATCATAGC<br>CTCTGCTTCTACTACCGGCGTCTGGGTCCCTTACTTCCCACGAGTGCGGCACCAAGTACAGCCCTCACCTCCTCTACTGGGACCTGCCAGGGC<br>TGCGTCCTAACCGGCGTCTGGGTCCCTTACTTCCCACGAGTGCGGCACCAAGTACAGCCCTCACCTCCTCTACTGGGACCTGCCAGGGC<br>TCCACTCCTTCCTCCTCGTCCCTTACTTCTCTGAAGTACGGCAAGTATCATGACCCACCGTCCACAACGCCAACACTGCTCCCTCGAGACGAAGTGTT<br>TCCCCCAAGAAGAGTCAGAACATCAAGTGTACGGCAAGTACCTGACGGACGCTGCACATTCCACCCACCGTTAACGGTTCACTCTC<br>GGCTGGCCTTTGTACTTAGCCTTCAACGTCTCGGGGAGACCTTACGACGGACGCTGCATCCTCGCCGTCTTAGTTTTGATCACTTGCACCACAACAAGGTCTTCCACAATATCACG<br>ACCGGCGAGCGTTCTCCAGATATACATCTCCGACGGTCTGATTGTCAACGGATACGGATCCACCATGCCGAATCTTGAACAAAGGTCTTCCACAATATCACG<br>GATGGTTCGCTTCGTCTGAGTGGGATTGGTTGAGGGGAGCTTTGGCCACCGTCGACCACTGGGAAGGTCTAAGGGCCGATGTTGCAGGACGAGTATA<br>TATGACTCGTCTGAGTGGGATTGGTTGAGGGGAGCTTTGGCCACCGTCGACCATGCCGAATCTTGAACAAAGGTCTTGCAGACGAGTATA<br>ACACGCCACGTGGCGCATCACCTGTTCTCGACCATGCCGACGATGGTTAAGGGACGATGGTGAGGAGGGTGTATCTATGTGAACCGAACTGGAGAAGGT<br>TCAGTTCGATGGACGCTGGTTAAGGCGGATGTGGAGGAGGGGAGGCGATGGTGAGGAGGGTGTATCTATGTGAACCGAACTGGAAGAAGGT<br>GTGTTCTCGTACAACAATAAGTTATGA |
| SEQ ID NO 2 | MGAGGRMQVSPPSKKSETDNIKRVPCETPPFTVGELKKAIPPHCFKRSIPRSFSYLLIWDIIIASCFYYVATTYPPLLPHPLSYFAWPLYWACQGC<br>VLITGVWLIAHEGGHHAFSDYQWLDDTVGLIPHSFLLVPSYHSFLSWKYSHRRHSNTGSLERDEVFVPKKKSDIKWYGKYLNNPLGRTVMLTVQFFLGW<br>PLYLAFNVSGRPYDGGFACHFHFNAPIYNDRERLQIYISDAGILAVCYGLYRYAAVQGVASMWCFYGVPLLIVNGFLVLITYLQHTHPSLPHYDS<br>SEWDWLRGALATVDRDYGILNKVFHNITDTHVAHHLFSTMPHYHAMEAFKAIKPILGEYYQFDGTPVVKAMWREAKECLYVEPDRQGEKKGVFWY<br>NNKL |
| SEQ ID NO 3 | ATGGGTGCAGGTGGAAGAATGCAAGTGTCTCCTCCCTCCAAAAAGTCTGAAACCCGACAACATCAAGCGCGTACCCTGCGAGACACCGCCTTCAC<br>TGTCGGAGAACTCAAGAAAGCAATCCACTACCGCTCGGCACCAGTGTTCAAACGCTGATCCGTCTCTTCTCGACCGTCTGGACATCATATAGCCT<br>CCTGCTTCTACTACCGGCTCTGGGTCTGGAGTGAGTGATGGTGGCACCAAGCTACCAGCTCCTCTACTCGGCCTGCAGGGCTGCG<br>CCCTAACCGGCGTCTGGGTCCATAGCCACCGAGTCGCGACCACCGAGCTATGACGTCTGAGACAGCCACCATTCAACACTGCTCCCTCGCTATCTCCAC<br>TCCTTCCTCCGTCCCTTACTTCTCTGAACTACAGTACAGCCAAGTACCTGACGGACGCTGCACATTCCACCCACCGTCAACGGTTCACTCCTCTCC<br>CAAGAAGAGTCAGAACATCAAGTGTACGGCAAGTACCTTACGACGCACCTTTGCCACTCACTTACTTCGACGGACGCTGCACATCTACAACGACCGTGGC<br>CTTTGTACTTAGCCTTCAACGTCTCGGGGAGACCTACGACGGCATCCTGACGGTCTTGCATCACTTACTGGACACACTTGAACAAGGTCTGTCAAGGAGTTGCCTGATGGTCTG<br>CGTCTCCAGATATACATCTCCGACGGCATCCTGGCAGTCTGTCAACGGGTTCTTAGTTTGATCACTTACTTGCAGCACGACGCAATCCTTCCCTGCCTCACTATGACTCGT<br>CTGAGTGGGATTGGTTTGAGGGGAGCTTTTGGCCACCGTTGACACAGACATCTGAACAGGTCTTCCAACAATATCACGGACAGCACGGTG<br>GCCATCACCTGTTCTCGACCATGCCGCATTATCACCGGAAGCCGATGGAAGCTACGAAGGCGATAAGCCGACACCGAAGGTGAGAAGAAGGTGTGTTCTGGTACA<br>GACGCCGGTGCTTGGTTAAGGCGATGTGGAGGAGGCGAAGAGTGTATCTATGTGAAACCGACCAAGGTGAGAAGAAGGTGTGTTCTGGTACA<br>ACAATAAGTTATGA |
| SEQ ID NO 4 | MGAGGRMQVSPPSKKSETDNIKRVPCETPPFTVGELKKAIPPHCFKRSIPRSFSYLIWDIIIASCFYYVATITSLSSLTLSPTSPGLSTGPARAA<br>S |

FIG. 1B

| SEQ ID NO 5 | ATGGGTGCAGGTGGAAGAATGCAAGTGTCTCCTCCCTCCAAGAAGTCTGAAACCGACATCAAGCGCGTACCCTGAGACACCGCCCTTCAC<br>TGTCTGGAGAACTCTACTACGCTGGGTCTGCCCTTACTTCCCTCGATCCCTGTTCAAACGTCCACTCATCTCCTCATCTGGGACATCATCATCATAGCCT<br>CCTGCTTCTACTACGGCGTCTGGGTCTGCCCTTACTTCTCCTGGAAGTACAGTCATAGCCCACGCGCCTCAGCGACTACCAGTGGCTTGACGACACCGTCGGTCTCATCTTCCA<br>GTCCTAACCGGCGTCTGGGTCTGCCCTTACTTCTCCTGGAAGTACAGTCATAGCCCACGCGCCTCAGCGACTACCAGTGGCTTGACGACACCGTCGGTCTCATCTTCCA<br>CTCCTTCCTCCTCGTCCTACTTCTCCTGGAAGTACAGTCATAGCCCACGCGCCTCAGCGACTACCAGTGGCTTGACGACACCGTCGGTCTCATCTTCCA<br>CCAAGAAGAAGTCAGACATCAAGCGGTACGGCAAGTACCTTACGACAACCCTTGGGACGACCGGCTTGATGTTAACGGTTCACTCGGCTGG<br>CCGTTGTACTTAGCCTTCAACGTCTCGGGAAGACCCTTACGACAGTCCATCCTGCTTGCCATTCACCCTGCTTACGTCTTCTTCCTGTTACGGCACACGCATCCTTCCGTTACGGCCATCCTCCGTTACGGCACAACGCCGGGA<br>GCGTCTCCAGATATACATCTCCGACGCTGGCATCAATGGTTCCTCGTGTTGATCACTTACTCGGAGCACACAAGGTCTTCCACAATATTACGACACGCACGT<br>GCTCTACGAGTGCCCGCTTCTGAGGGGAGCTTTGGCTACCCGTTGGCTACCCGTTGACAGAGACTACGAGCTACCAGTCTTGAACAAGCCGATAAAGCCGATAAAGCCGATTATCAGTTCGATG<br>GGACGCGGTGGTTAAGGCGATGTGGAGGGAAGGAGAGTGTATCTATGTGAACCAGGCAAGGTGAGAAGAAGGTGTGTCTGGTAC<br>AACAATAAGTTATGA |
| SEQ ID NO 6 | MGAGGRMQVSPPSKKSETDTIKRVPCETPFFTVGELKKAIPPHCFKRSIPRSFSYLIWDIIIASCFYYVATTYFPLLFHPLSYFAWPLYWACQGC<br>VLITGVWVIAHECGHHAFSDYQWLDDTVGLIFHSFLLVPYFSWKYSHRRHHSNTGSLERDEVFVPKKKKSDIKWYGKYLNNPLGRTVMLITVQPTLGW<br>PLYLAFNVSGRPYDGGFACHFHPNAPIYNDRERLQIYISDAGILAVCYGLFRYYAAAQGVASMVCFYGVPLLIVNGFLVLITYLQHTPSLPHYDS<br>SEWDWLRGALATVDRDYGILNKVFHNITDTHVAHHLFSTMPHYHAMEATKAIKPILGEYYQPDGTPVVKAMREAKECIYVEPDRQGEKKGVFWY<br>NNKL |
| SEQ ID NO 7 | ATGGGTGCAGGTGGAAGAATGCAAGTGTCTCCTCCCTCCAAGAAGTCTGAAACCGACATCAAGCGCGTACCCTGAGACACCGCCCTTCAC<br>TGTCTGGAGAACTCTACTACGCTGGGTCTGCCCTTACTTCCCTCGATCCCTGTTCAAACGTCCACTCATCTCCTCATCTGGGACATCATCATCATAGCCT<br>CCTGCTTCTACTACGGCGTCTGGGTCTGCCCTTACTTCTCCTGGAAGTACAGTCATAGCCCACGCGCCTCAGCGACTACCAGTGGCTTGACGACACCGTCGGTCTCATCTTCCA<br>GTCCTAACCGGCGTCTGGGTCTGCCCTTACTTCTCCTGGAAGTACAGTCATAGCCCACGCGCCTCAGCGACTACCAGTGGCTTGACGACACCGTCGGTCTCATCTTCCA<br>CTCCTTCCTCCTCGTCCTACTTCTCCTGGAAGTACAGTCATAGCCCACGCGCCTCAGCGACTACCAGTGGCTTGACGACACCGTCGGTCTCATCTTCCA<br>CCAAGAAGAAGTCAGACATCAAGCGGTACGGCAAGTACCTTACGACAACCCTTGGGACGACCGGCTTGATGTTAACGGTTCACTCGGCTGG<br>CCGTTGTACTTAGCCTTCAACGTCTCGGGAAGACCCTTACGACAGTCCATCCTGCTTGCCATTCACCCTGCTTACGTCTTCTTCCTGTTACGGCACACGCATCCTTCCGTTACGGCCATCCTCCGTTACGGCACAACGCCGGGA<br>GCGTCTCCAGATATACATCTCCGACGCTGGCATCAATGGTTCCTCGTGTTGATCACTTACTCGGAGCACACAAGGTCTTCCACAATATTACGACACGCACGT<br>GCTCTACGAGTGCCCGCTTCTGAGGGGAGCTTTGGCTACCCGTTGGCTACCCGTTGACAGAGACTACGAGCTACCAGTCTTGAACAAGCCGATAAAGCCGATAAAGCCGATTATCAGTTCGATG<br>GGACGCGGTGGTTAAGGCGATGTGGAGGGAAGGAGAGTGTATCTATGTGAACCAGGCAAGGTGAGAAGAAGGTGTGTCTGGTAC<br>AACAATAAGTTATGA |
| SEQ ID NO 8 | MGAGGRMQVSPPSKKSETDTIKRVPCETPFFTVGELKKAIPPHCFKRSIPRSFSYLIWDIIIASCFYYVATTYFPLLFHPLSYFAWPLYWACQGC<br>VLITGVWVIAHECGHHAFSDYQWLDDTVGLIFHSFLLVPYFSWKYSHRRHHSNTGSLERDEVFVPKKKKSDIKWYGKYLNNPLGRTVMLITVQPTLGW<br>PLYLAFNVSGRPYDGGFACHFHPNAPIYNDRERLQIYISDAGILAVCYGLFRYYAAAQGVASMVCFYGVPLLIVNGFLVLITYLQHTPSLPHYDS<br>SEWDWLRGALATVDRDYGILNKVFHNITDTHVAHHLFSTMPHYHAMEATKAIKPILGEYYQPDGTPVVKAMREAKECIYVEPDRQGEKKGVFWY<br>NNKL |

FIG. 1C

| SEQ ID NO 9 | AGAGAGAGAAGGAGGAGACAGAGAGAGAGTTTGAGGAGGAGCTTCTTCGTAGGGTTCATCGTTATTATCGTTAATCTTGATCCCCCCTACGT |
|---|---|
| | CAGCCAGCTCGAAGGTCCCCTTTCTCTTCTTCCATTTCTTCCTCCATTTTACGTTGTTTCAATCTTGGTCTGTTCTTTATCGCTTTCTGTTCTAT |
| | CTATCATTTTTGCATTTCAGTCGATTTAATTCTAGATCTGTTAATATTATTTATTCATTAAACTATAGATCTGATTCTCTGTTTTCATGTG |
| | TGAAATCTTGATGCTGTCTTTACCATTAATCGATTATATTGTCTATACCGTGGAGAATATGAAAAGTTGCATTTCATTTGTCCGAATACAAAC |
| | TGTTTGACTTTCAATCTTTTTAATGATTATTTTGATGGGTTGGTGGAGTTGAAAAATCACCATAGCAGTCTCACCTCCTGTCTTAGAATATAT |
| | CCTTCCTATTCAAAGTTATATATATTTGTTACTTGTCTTAGATCTGGAACTCGAGACATGTAAGTACCTATTTGTTGAAGTCTTTGGGTAAAAAAC |
| | TTATGTCTCTGGGTAAAATTTGCTTGACCGATTCCTATTGGCTTCGATTCTGTAGTTACCTAATACATCGAAAAAGTTTCATTTGGC |
| | CTATGCTCACTTCATGCTTACAAACTTTCTTTGCAAATTAAATTCAGATTTCTCATAGATTCAGATGCAATAGATTTGCATGAGAAA |
| | ATAATAGGATTCATGACAGTTAAAAAAGATTGTATTTTGTTGTTTGTTTATCGTTTAAAAGTCTATATGTTGACAATAGAGTTGCTCTCAACTGT |
| | TTCATTTAGCTTTTTGTTTTTGTCAAGTTGCTTATTCTTAGAGACATTGTGATTATGACTTGTCTTCTCTAACGTAGTTTAGTAATAAAGACGA |
| | AAGAAATTGATATCCACAAGAAAGAGATTGTAAGCTGTAACGTATCAAAATCTCATTAATAACTAGTAGTATTCTCAACGCTATCGTTATTTCTTT |
| | CTTTGGTTTGCCACTATATAATTTGTTGGTTTAATTAACTTGAGTCTTTGCTTTGGTTATGCAGAAACATGGGGTGCAGGTGGAAGAATGCAAGTGTC |
| | TAACACTGAATATTAATTTGTTGGTTTAATTAACTTGAGTCTTTGCTTTGGTTATGCAGAAACATGGGGTGCAGGTGGAAGAATGCAAGTGTC |
| | TCCTCCCTCCAAAAGTCTGAAACGCGACACATTCGAAGCGCGTTACCCTGCGAGACACAGCGCCTTCACTGTCGGAGAACTCAAGAAACAATCCCAC |
| | CGCACTGTTTCAAACGCTCGATCCCTCGCTCTTTCTCCAGCATCATCAGTCGGGACATCATCAGGCTGTCCTCTAACCGCGCTCGGTCTCATGAGCCCA |
| | TTCCCTCCTCCCTCACCGCCTTCAGCGACTACCAGTTGGCTGGACTGGCTCCCTCCGAGACGACACCGTTGTCTCCATGGTTTGTCCCAAGAAGAACATCAGTCAGATCAAGTGGTAC |
| | CGAGTGCGGCCACCACGCCTTCGACGCCATTCGAGCGACTACCAGTTGGCTGGACTGGCTCCCTCCGAGACGACACCGTTGTCTCCATGGTTTGTCCCAAGAAGAACATCAGTCAGATCAAGTGGTAC |
| | GGAAGTACCTCAACAACCCTTTGGGACGCACCCGTGATGTTAACGGTTCAGTTCAGTTCACTCTCGGCCTTTGTACTTAGCCTTCAACGTCTCGGG |
| | GAGACCTTACGACGCGGCTTCGCTTGCATTTCCACCCCAACGTCTCCATTCTACAACGACCGTGAGCGTCTCAAGATATACATCCGACGCTG |
| | GCATCCTCGCCGTCTGCTACGGTCTCTACAGCACTTCGCAGGAGTTGCCTCCAGGAGTCGCCTGATGCTCGTTCTACCGGAGTTCCCTTCTGATTGTC |
| | AACGGGTTCTTAGTTTTGATCACTTACTTGCAGCACACACATCCTTCCCTGCCCACTATGACTGGTCGAGTGGGATTGGTTGAGGGAGCTTT |
| | GGCCACCGTTGACAGAGAACTACGGAATCTTGAACAAGCCGGATAAAAGCCGATACTGGGAGAGTATTATCAGTTCGACGCCATCACCTGTTCTCGACCATGCCGC |
| | ATTATCACGCGATGGAAGCTGTATCTATGTTGGAACCGGACAGGCCAAGCTGAATATCTGTTCTGGTACAACAATAAGTTATGAAGCAAAGAAGAAAC |
| | GAGGCAAGGAGTGTATCTTCTTGTTGCCTTTGTCTAAAATGTCTAAAATGTGTCTAAAATGTCTGTCTATTGTTCTCTTCTTGTTCTGTCTGACATTTT |
| | TGAACCTTTCTCCTTCTATGATGTTTGGAAGTTAGTCTAAAATGTCTAAAATGTCTGTCTATTGTTCTCTTCTTGTTCTGTCTGACATTTT |
| | GGCTAAAATTATGTGATGTTGGAAGTTAGTCTAAAATGTCTGTCTATTGTTCTCTTCTTGTTCTGTATGTTGGGATCGTGTTGAAA |
| | TGTGACTTTCGGACTAGTAGTCTTCTCTGTTCTCGAACT |

FIG. 1D

| SEQ ID NO 10 | GAGAAGAGAGAGAGAGAGAGAGAGAGAGAGAGAGTGAGTTTGAGGAGGAGCTTCTTCGTAGGGTTCATCGTTATTAACGTTAAATCTTCACCCCTA<br>CGTCAGCCAGCTCAAGGTCCCCTTTCTTCTCCATTCTTTTCATTCTACGTTGTTTTCAATCTTATGAAACTTTCTGGTCTGTGCTTTTCTTATC<br>GCTTTCTATTCTATCTATCATTTTGCATTTCAGTCGATTAATTCTAGATCTGTTAATATTAAACTATAGATCGTTCTTGATTCTCTGTTTT<br>CATGTGTGAAATCTGATGCTGTATTAATCGATTATATTGTCTATACCGTGGAGAATATCAAATGTGCATTTCATTTCTCCGAATACAAAGTG<br>TTTGACTTTCAATCGTTTTAATTATATATATATATATTTTGATGGTTGGTTGGAGTTGAAAAATCACCATAGCAGTCTCACGTCCTGGTT<br>TTAGAAATATCCTATTCAAAATCTATTATATTTACTTGTTTTAGATCTGGACCTGAGACATATAAGTTACCTATTTGTTGAGATCTTTGGGTAAA<br>AACTTATGCTCTCGGGTAAAATTGCTGGGAGATTTGACCGATTCCTATTGGCTCTTGATTCTGTAGTTACGGTAATACATGAAAAAGTTTCATTT<br>GGCCTATGCTCACTTCATGCTTATAAACGTTTCTTGCAAATTAATTGGATTAGATGTTATTTCATAGATTCAGTCATTCAGATACAATGGAGTT<br>GCAATGAAGACAAAATAATAGAATTCGTGACAGTAAAAAAGATTGTATTTTGTTTGTTTGTTTAAAAGTTGTCTTCTTTAACGTAGTTAGTAA<br>CTTCAACTGTTTCATTTAGCTTCTTTTTTGTCAAGTTGCTTATTCTTAGAGACATTGTGATTATGACATTGTCTTCTTTAACGTAGTTAGTAA<br>TAAAAGACGAAAAGAAATTGATATCCACAAGAAAAGAGATGTGAGCTGTAGCGTATCAAATCTCGTTCATTTACTAGTAGTATTCTCAACGCTATCG<br>TTTATTATTTTCTTCGTTGGTTTGCCACTATATGCCACTTCTCTCCTCTTTGTCCCACGTACTATCCATTTTTTTGTGTAGTCCATTTC<br>TTGTAACTTATATAACCTAACTCGTCGAATCTTTTGTCTCTGTAGATTAATTTGTTGGTTTAATTAAGTCTTTGCTTTTGCTTATGCAGA<br>AACATTGGGTGCAGGTGGAAGAATGCAAGTGTCTCTCCTCCAAGAAGTCTGAAACGACACCATCAAGCGCGTACCCTGCGAGACACGCCCTT<br>CACTGTCGCTTCTACTACGTCGCCACCACTTACTTCCCCTCGCTCTTCCACCCTCGCTCACTTCGCTGCCTCCCAATCTCGCCAAGGG<br>TGCGTCCTAACGGCGTCTGGGCATAGCGCCATGGCGGCCACCAGTGCGGCCCTTGCGACTACCAGTGGCTTGACGACACCGTCGGTCTCATCTT<br>CCACTCCTTCCTCGTCGTCGCCTTACTTCTCCTGGAAGTACAGTACGACTCATGCACGCCACCGTGATGTTAACGGTTCAGTTCACTCTCGGC<br>TCCCCAAGAAGAAGTCAGAACATCAAGTGGTACGGCAAGTGGTACCCAACCCTTTGGACGCCACCCGTCCCATCTCACCCAACGCTCCACCG<br>TGGCCGTTGTACTTAGCCTTCACGTCTCACCGTCTCGGGAAGACTTCCGACTGTTCCCGTGTTGACTTCAAGCTGCCATTTCCACCCAACCG<br>CGAGCCGTCTCAGATATACATCTCCGAGCGCTGGCATCTCCGCGTGTTGACTTCAATGGTTCCCGTGTTGATCAGTCAACCTGCTGCCACTACGAT<br>TCGTCCAGTGGGATTGGTTGAGGGAGCTTGGCTACCGGTTGACAGAGACTACGAAGCTCTTGAACAAGGTCTTCCACAATATTACCACACGCA<br>CGTGGCGCATCATCTGTTCTCCACGAGCCGCCATTATGACGCGGATGAAGCTACAAGGCGATAAGCCGATAAAAGCCGATATCAGTTCG<br>ATGGGACGCCGCGTGGTTAAGGACGATGTGAGGGAGGCGAAGGAGTGTATCTATCTGCAACCGACAAGCAAGGTGAGAAGAAAGTGTGTTCTGG<br>TACAACAATAAGTTATGCAGGCGATTATGATGATGTGAAAGAACAAAGAAGATATTGTCACGAACCTTTCTCTTGCTGTCCTGGTCGTCTTTGTTTT<br>AAGAAGCTATGTTTTCGTTTCAATAATCTTAATCATTTTGTGTTTTCTGACATTTTGGCTAAAATTATGTGATGTTGGAAGTTAGTGT<br>CTAAAATGTCTTGTCTGTATTGTCTTCTCCATCGCGTGTTATGTTTGGGATCGTTGAAATGTGACCTTTCGGACCAGTGAACTCTTGGTTCT<br>CGAACT |

| SEQ ID NO 11 | GAGAACCAGAGAGATTCATTACCAAAGAGAGATAGAGAGAGAGAAAGAGGAGACAGAGAGAGAGTTTGAGGAGGAGCTTCTTCGTAGGGTTC
ATCGTTATTAACGTTAAATCTTCATCCCCCCTACGTCAGCCAGCTCAAGAGAACATGGGTGCAGGTGGAAGAATGCAAGTGTCCTCCCTCCA
AAAAGTCTGAAACCGACAACATCAAGCGCGTACCCTGCGAGACACCTGACTGTCGGAGAACTCAAGAGAAGCAATCCCACCGACTGTTT
CAAACGCTCGATCCCTCGCTCTTCTCCTACTCCATCTGGACATCATCATAGCCTTCTACTACGTCGGCCACCACTTACTTCCCTCTC
CTCCCTCACCCCTCTCTACTTCGCCTGGCCTCTACTTGGAGCTGCTGGGCCTGGCCTCCTAACGGGCTGCGTCCTAACCGGACGTCTGGGTCATAGCCACGAGTGCG
GCCACCACGCCTTCAGCGACTACCAGTGGCTGGACACGACACCGTCGGAGCCCTTCATCTTCGTCCGTTACTTCTCCTGAAGTA
CAGTCATCGACGCCAACCATTCCAACACTGGCTCCCGTGATGTTAACGGTCAGTTCACTCTCCGGCTTGTACTTAGCCTTCAACGTCGGGGAGAC
TACTCAACACACCCTTGGGACGGCACCCGTGATGTTAACGGTCAGTTCACTCTCCGGCTTGTACTTAGCCTTCAACGTCGGGGAGAC
CTTACGACGGCGCCTTCCCAATTTCCCACCGGAAGTTCCCATCTCAACGGACCCCCGTGAGCCGTCTCCAGATATACATCTCCGACCTGGCAT
CCTCGCCGTCTGCTACTACGTCTGCTCTGCCACACGCATCCTTCCCCTGCTCCTCCACTATATCACGGACACGCACGTGGCGCACGTGGCCATCACCTCGTCTCGACCATGCCGCA
GGGTTCTTAGTTTTGAATCACTTACTTGCAGCACTGAATCTTGAACAAGGTCTTCCACACAATATCACGGACACGCACGTGGCCATCACCTCGTCTCGACCATGCCGCA
CCACGGTTGACAGAGACTACGGAATCTTGAACAAGGTCTTCCACACAATATCACGGACACGCACGTGGCCATCACCTCGTCTCGACCATGCCGCA
TATCATGCGATGGAAGCTGTATCTATGTGGAACCCGACGGCGATTAAAGCCCGATACTCGGAGAGTATATCAGTTCGTGCTGGTACAACAATAAGTTATGAAGCAAGAAGAAA
GAGGCGAAGGAGTGTATCTATGTGGAACCCGACGGCGATTAAAGCCCGATACTCGGAGAGTATATCAGTTCGTGCTGGTACAACAATAAGTTATGAAGCAAGAAGAAA
CTGAACCTTTAGTTTTGTTTAAGAAGCTATGATGTTAAGAAGCTATGTTAGTGTCCTAAAATGTCTAAAATGAAGCGTCGTTCTTCATCGCTGTTATGTTTCTGACA
TTTTGCCTAAATTATGTGATGTTGGAAGTTAGTGTCCTAAAATGTCTTGTTCTCGAACTCTTGTTCTCGAACTAAAAAAAAAAAAAAA
TGAAATGTGACTTTCGACTAGTGAACTCTTGTTCTCGAACTAAAAAAAAAAAAAAA |
| SEQ ID NO 12 | GAGACCAGAGATTCATTACCAAAGAGAGATAGAGAGAGAGAAAGAGGAGAGAGTGAGTTTGAGGAGGAGCTTCTTCGTAGGGTTCATCG
TTATTAACGTTAAATCTTCACCCCGTAGCAGCCAGCTCAAGAGAACATGGGTGCAGGTGGAAGAATGCAAGTGTCCTCCCCAAGAAGTCT
GAAACCGACAACATCAAGCGCGTACCCTGACTCGGAGACACCGTCACTGTCGGAGAACTCAAGAGAACTCAAGAAAGCAATCCCACGACTGTTTCAAACGCTC
GATCCCTCGCTCTTCTCGCCTGGCCTCTACTTGGACATCATCAGCCTTCTACTACGTCGGCCACCACTTACTTCCCTCCTCCACC
CTCTCCTCCTACTTGCGCTGGCCCTCTCTACTTGGCCTGTGCCTGCGCTGGGTCATAGGGTCTATAGGGCTCATGGGCTCTAACCGGGTCTGGGTCATAGCCACGAGCC
TTCAGCGACTACCAGTGGCTTGAGCACACTGGCCTCCGTCGGTTCAGTCACTCTGCCCTTCATCTTCGTCGGCCGTTCAAGCGGAAGTACAGTCATCGACG
CCACCATTGCAACACTGCTCCCTGCAGAGAAGAAGTTCAGTGATCAGATAAGGTTACGGCGAAGCTACCTCGACAACGGACTGAACGCTGAACATCAAGCGCAACCTCAACAACC
CTTTGGGACGGCACCGTGATGTTAACGGTTCAGTTCAGTCACTCTACGATATACATCTCCGACCGGCTGGGCATCGGGCGGCGCAAACG
TTCGCTTGCCATTTCCACCCCAACCGGCCGCCGGGGCCCAGGGAGTGGCCCTCAGGGCTCTGCTTCTACGGAGCTCGGATGCGATCTCGGCGATCGCAGGCGTTCCTCGTTGA
CGGTCTTCTTCCGTTACGGCCGCCGGGCCCAGGGAGTGGCCTCAGGGCTCTGCTTCTACGGAGTTCCCGACGATCGCAGCGTGGAGCTCGGATGGAAGC
TACTTACTTGCAGCACCGCATCCTTCCCTGCCCTACGATTCGTCCGACGATTGGTTGAGGGGACGTTTGCAGCGCTGAGAGAC
TACGAATCTTGAACAAGGGCTGCCACATAAGGATCATATCTACGATTGGTTGAGGGGACGTTTGCAGCGCTGAGAGAC
TACCAAGGCGATAAAGCCGATACTCGGAGAGTATTATCAGTTCGATGGGGACGCCGGTGGTGGAGGCGAAAACCTTATCTTCTTCCTATG
ATGTGGAACCGGACAGGCAAGGTGAGAAGAAGTGTTCGTGCTCGTCGATATCACACAATAAGTTATGAGGATTRRAAGAAACTGAACCTTATGGATTAT
TGGAAGTTAGTGTCTAAAATGTCTGTCTGTATCATCCATTTTGTTTAAGAAATCTGTTATGTTTAGGGATCGTTGAAATGAGATCTTGAATGTGATGT
AACTCTTGTTCTCGAACTAAAAAAAAAAAAAAAA |

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Monsanto SAS
Centre de Recherche de Boissay
28310 Toury
France

RECEIPT IN THE CASE OF AN ORIGINAL DEPOSIT
issued pursuant to Rule 7.1 by the
INTERNATIONAL DEPOSITARY AUTHORITY
identified at the bottom of this page

NAME AND ADDRESS OF DEPOSITOR

| I. IDENTIFICATION OF THE MICROORGANISM | |
|---|---|
| Identification reference given by the DEPOSITOR: | Accession number given by the INTERNATIONAL DEPOSITARY AUTHORITY: |
| *Brassica napus.* CV Oleifera (METZG) MSP05 | NCIMB 41233 |

II. SCIENTIFIC DESCRIPTION AND/OR PROPOSED TAXONOMIC DESIGNATION

The microorganism identified under I above was accompanied by:

[ ] a scientific description

[X] a proposed taxonomic designation (Mark with a cross where applicable)

III. RECEIPT AND ACCEPTANCE

This International Depositary Authority accepts the microorganism identified under I above, which was received by it on
9 July 2004 (date of the original deposit)[1]

IV. RECEIPT OF REQUEST FOR CONVERSION

The microorganism identified under I above was received by this International Depositary Authority on
(date of the original deposit) and a request to convert the original deposit to a deposit under the Budapest Treaty was received
by it on
(date of receipt of request for conversion)

V. INTERNATIONAL DEPOSITARY AUTHORITY

| Name: NCIMB Ltd., | Signature(s) of person(s) having the power to represent the International Depositary Authority or of authorised official(s): |
|---|---|
| Address: 23 St Machar Drive Aberdeen AB24 3RY Scotland, UK | Date: 19 July 2004 |

[1] Where Rule 6/4(d) applies, such date is the date on which the status of International Depositary Authority was acquired.

Form BP/4 (sole page)

Fig. 2a

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Monsanto SAS
Centre de Recherche de Boissay
28310 Toury
France

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE<br>Address: | Accession number given by the<br>INTERNATIONAL DEPOSITARY AUTHORITY:<br>NCIMB 41233<br>Date of the deposit or of the transfer[1]:<br>9 July 2004 |

| III. VIABILITY STATEMENT |
|---|
| The viability of the microorganism identified under II above was tested on 9 July 2004 [2]. On that date, the said microorganism was:<br><br>[X] [3] viable<br><br>[ ] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

Fig. 2b

| IV. | CONDITIONS UNDER WHICH THE VIABILITY TEST HAS BEEN PERFORMED[4] |
|---|---|

| V. | INTERNATIONAL DEPOSITARY AUTHORITY |
|---|---|

Name: NCIMB Ltd.,

Address: 23 St Machar Drive
Aberdeen
AB24 3RY
Scotland

Signature(s) of person(s) having the power to represent the International Depositary Authority or of authorised official(s):

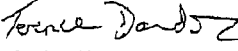

Date: 19 July 2004

[4] Fill in if the information has been requested and if the results of the test were negative.

Form BP/9 (second and last page)

Fig. 2c

BUDAPEST TREATY ON THE INTERNATIONAL
RECOGNITION OF THE DEPOSIT OF MICROORGANISMS
FOR THE PURPOSES OF PATENT PROCEDURE

Monsanto S.A.S.
Centre de Recherche de Boissay
28310 Toury
France

INTERNATIONAL FORM

RECEIPT IN THE CASE OF AN ORIGINAL DEPOSIT
issued pursuant to Rule 7.1 by the
INTERNATIONAL DEPOSITARY AUTHORITY
identified at the bottom of this page

NAME AND ADDRESS OF DEPOSITOR

| I. IDENTIFICATION OF THE MICROORGANISM | |
|---|---|
| Identification reference given by the DEPOSITOR: | Accession number given by the INTERNATIONAL DEPOSITARY AUTHORITY: |
| *Brassica napus* CV Oleifera (METZG) 28-DHS.086 | NCIMB 41365 |

| II. SCIENTIFIC DESCRIPTION AND/OR PROPOSED TAXONOMIC DESIGNATION |
|---|
| The microorganism identified under I above was accompanied by:<br>☐ a scientific description<br>☒ a proposed taxonomic designation<br>(Mark with a cross where applicable) |

| III. RECEIPT AND ACCEPTANCE |
|---|
| This International Depositary Authority accepts the microorganism identified under I above, which was received by it on 22 December 2005 (date of the original deposit)[1] |

| IV. RECEIPT OF REQUEST FOR CONVERSION |
|---|
| The microorganism identified under I above was received by this International Depositary Authority on (date of the original deposit) and a request to convert the original deposit to a deposit under the Budapest Treaty was received by it on (date of receipt of request for conversion) |

| V. INTERNATIONAL DEPOSITARY AUTHORITY | |
|---|---|
| Name: NCIMB Ltd.,<br>Ferguson Building<br>Craibstone Estate<br>Address: Bucksburn<br>Aberdeen,<br>AB21 9YA,<br>Scotland. | Signature(s) of person(s) having the power to represent the International Depositary Authority or of authorised official(s):<br><br>Date: 4 January 2006 |

[1] Where Rule 6/4(d) applies, such date is the date on which the status of International Depositary Authority was acquired.

Form BP/4 (sole page)

Fig. 2d

BUDAPEST TREATY ON THE INTERNATIONAL
RECOGNITION OF THE DEPOSIT OF MICROORGANISMS
FOR THE PURPOSES OF PATENT PROCEDURE

Monsanto S.A.S
Centre de Recherche de Boissay
28310 Toury
France

NAME AND ADDRESS OF THE PARTY
TO WHOM THE VIABILITY STATEMENT
IS ISSUED

INTERNATIONAL FORM

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name:<br>AS ABOVE<br>Address: | Accession number given by the<br>INTERNATIONAL DEPOSITARY AUTHORITY:<br>NCIMB 41365<br>Date of the deposit or of the transfer[1]:<br>22 December 2005 |

III. VIABILITY STATEMENT

The viability of the microorganism identified under II above was tested on 5 January 2006 [2]. On that date, the said microorganism was:

[X] viable

[ ] no longer viable

---

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

Fig. 2e

| IV. CONDITIONS UNDER WHICH THE VIABILITY TEST HAS BEEN PERFORMED[4] |
|---|
| |
| V. INTERNATIONAL DEPOSITARY AUTHORITY |

| | |
|---|---|
| Name: NCIMB Ltd., Ferguson Building<br>Address Craibstone Estate<br>Bucksburn<br>Aberdeen,<br>AB21 9YA,<br>Scotland. | Signature(s) of person(s) having the power to represent the International Depositary<br><br>Date: 16 January 2006 |

[4] Fill in if the information has been requested and if the results of the test were negative.

Form BP/9 (second and last page)

Fig. 2f

BUDAPEST TREATY ON THE INTERNATIONAL
RECOGNITION OF THE DEPOSIT OF MICROORGANISMS
FOR THE PURPOSES OF PATENT PROCEDURE

Monsanto S.A.S
Centre de Recherche de Boissay
28310 Toury
France

INTERNATIONAL FORM

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name:<br>    AS ABOVE<br>Address: | Accession number given by the<br>INTERNATIONAL DEPOSITARY AUTHORITY:<br><br>NCIMB 41374<br><br>Date of the deposit or of the transfer[1]:<br><br>10 February 2006 |

III. VIABILITY STATEMENT

The viability of the microorganism identified under II above was tested on 10 February 2006 [2]. On that date, the said microorganism was:

[X] viable [3]

[ ] no longer viable [3]

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

*Form BP/9 (first page)*

Fig. 2h

| IV. | CONDITIONS UNDER WHICH THE VIABILITY TEST HAS BEEN PERFORMED[4] |
|---|---|

| V. | INTERNATIONAL DEPOSITARY AUTHORITY |
|---|---|
| Name: NCIMB Ltd.,<br>Ferguson Building<br>Address Craibstone Estate<br>Bucksburn<br>Aberdeen,<br>AB21 9YA,<br>Scotland. | Signature(s) of person(s) having the power to represent the International Depositary<br><br>Date: 27 February 2006 |

[4] Fill in if the information has been requested and if the results of the test were negative.

Form BP/9 (second and last page)

Fig. 2i

SEQUENCE LISTING

<160> NUMBER OF SEQ ID NOS: 12

<210> SEQ ID NO 1
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 1

```
atg ggt gca ggt gga aga atg caa gtg tct cct ccc tcc aaa aag tct      48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
            20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
        35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
    50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg cct ttg     576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct     624
Tyr Leu Ala Phe Asn Val Ser Gly Arg Pro Tyr Asp Gly Gly Phe Ala
        195                 200                 205
```

| | | |
|---|---|---|
| tgc cat ttc cac ccc aac gct ccc atc tac aac gac cgt gag cgt ctc<br>Cys His Phe His Pro Asn Ala Pro Ile Tyr Asn Asp Arg Glu Arg Leu<br>210                215                220 | | 672 |
| cag ata tac atc tcc gac gct ggc atc ctc gcc gtc tgc tac ggt ctc<br>Gln Ile Tyr Ile Ser Asp Ala Gly Ile Leu Ala Val Cys Tyr Gly Leu<br>225                230                235                240 | | 720 |
| tac cgc tac gct gct gtc caa gga gtt gcc tcg atg gtc tgc ttc tac<br>Tyr Arg Tyr Ala Ala Val Gln Gly Val Ala Ser Met Val Cys Phe Tyr<br>               245                250                255 | | 768 |
| gga gtt cct ctt ctg att gtc aac ggg ttc tta gtt ttg atc act tac<br>Gly Val Pro Leu Leu Ile Val Asn Gly Phe Leu Val Leu Ile Thr Tyr<br>260                265                270 | | 816 |
| ttg cag cac acg cat cct tcc ctg cct cac tat gac tcg tct gag tgg<br>Leu Gln His Thr His Pro Ser Leu Pro His Tyr Asp Ser Ser Glu Trp<br>       275                280                285 | | 864 |
| gat tgg ttg agg gga gct ttg gcc acc gtt gac aga gac tac gga atc<br>Asp Trp Leu Arg Gly Ala Leu Ala Thr Val Asp Arg Asp Tyr Gly Ile<br>290                295                300 | | 912 |
| ttg aac aag gtc ttc cac aat atc acg gac acg cac gtg gcg cat cac<br>Leu Asn Lys Val Phe His Asn Ile Thr Asp Thr His Val Ala His His<br>305                310                315                320 | | 960 |
| ctg ttc tcg acc atg ccg cat tat cac gcg atg gaa gct acg aag gcg<br>Leu Phe Ser Thr Met Pro His Tyr His Ala Met Glu Ala Thr Lys Ala<br>               325                330                335 | | 1008 |
| ata aag ccg ata ctg gga gag tat tat cag ttc gat ggg acg ccg gtg<br>Ile Lys Pro Ile Leu Gly Glu Tyr Tyr Gln Phe Asp Gly Thr Pro Val<br>               340                345                350 | | 1056 |
| gtt aag gcg atg tgg agg gag gcg aag gag tgt atc tat gtg gaa ccg<br>Val Lys Ala Met Trp Arg Glu Ala Lys Glu Cys Ile Tyr Val Glu Pro<br>               355                360                365 | | 1104 |
| gac agg caa ggt gag aag aaa ggt gtg ttc tgg tac aac aat aag tta<br>Asp Arg Gln Gly Glu Lys Lys Gly Val Phe Trp Tyr Asn Asn Lys Leu<br>370                375                380 | | 1152 |
| tga | | 1155 |

<210> SEQ ID NO 2
<211> LENGTH: 384
<212> TYPE: PRT
<213> ORGANISM: Brassica napus

<400> SEQUENCE: 2

Met Gly Ala Gly Gly Arg Met Gln Val Ser Pro Pro Ser Lys Lys Ser
1                5                    10                15

Glu Thr Asp Asn Ile Lys Arg Val Pro Cys Glu Thr Pro Pro Phe Thr
               20                    25                30

Val Gly Glu Leu Lys Lys Ala Ile Pro Pro His Cys Phe Lys Arg Ser
                 35                    40                45

Ile Pro Arg Ser Phe Ser Tyr Leu Ile Trp Asp Ile Ile Ala Ser
50                55                60

Cys Phe Tyr Tyr Val Ala Thr Thr Tyr Phe Pro Leu Leu Pro His Pro
65                70                75                80

Leu Ser Tyr Phe Ala Trp Pro Leu Tyr Trp Ala Cys Gln Gly Cys Val
                 85                    90                95

Leu Thr Gly Val Trp Val Ile Ala His Glu Cys Gly His His Ala Phe
               100                105                110

Ser Asp Tyr Gln Trp Leu Asp Asp Thr Val Gly Leu Ile Phe His Ser
               115                120                125

Phe Leu Leu Val Pro Tyr Phe Ser Trp Lys Tyr Ser His Arg Arg His

```
                130                 135                 140
His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
                195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
370                 375                 380

<210> SEQ ID NO 3
<211> LENGTH: 1154
<212> TYPE: DNA
<213> ORGANISM: Brassica napus
<220> FEATURE:
<221> NAME/KEY: CDS
<222> LOCATION: (1)..(291)

<400> SEQUENCE: 3 atg ggt gca ggt gga aga atg caa gtg tct cct ccc tcc aaa aag tct     48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act     96
Glu Thr Asp Asn Ile Lys Arg Val Pro Cys Glu Thr Pro Pro Phe Thr
            20                  25                  30 gtc gga gaa ctc aag aaa gca atc cca ccg cac tgt ttc aaa cgc tcg    144
Val Gly Glu Leu Lys Lys Ala Ile Pro Pro His Cys Phe Lys Arg Ser
        35                  40                  45 atc cct cgc tct ttc tcc tac ctc atc tgg gac atc atc ata gcc tcc    192
Ile Pro Arg Ser Phe Ser Tyr Leu Ile Trp Asp Ile Ile Ile Ala Ser
    50                  55                  60 tgc ttc tac tac gtc gcc acc att act tcc ctc tcc tcc ctc acc ctc    240
Cys Phe Tyr Tyr Val Ala Thr Ile Thr Ser Leu Ser Ser Leu Thr Leu
65                  70                  75                  80 tct cct act tcg cct ggc ctc tct act ggg cct gcc agg gct gcg tcc    288
Ser Pro Thr Ser Pro Gly Leu Ser Thr Gly Pro Ala Arg Ala Ala Ser
```

-continued

```
                   85                  90                  95
taa ccggcgtctg ggtcatagcc cacgagtgcg gccaccacgc cttcagcgac       341
taccagtggc tggacgacac cgtcggcctc atcttccact ccttcctcct cgtcccttac   401
ttctcctgga agtacagtca tcgacgccac cattccaaca ctggctccct cgagagagac   461
gaagtgtttg tccccaagaa gaagtcagac atcaagtggt acggcaagta cctcaacaac   521
cctttgggac gcaccgtgat gttaacggtt cagttcactc tcggctggcc tttgtactta   581
gccttcaacg tctcggggag accttacgac ggcggcttcg cttgccattt ccaccccaac   641
gctcccatct acaacgaccg tgagcgtctc cagatataca tctccgacgc tggcatcctc   701
gccgtctgct acggtctcta ccgctacgct gctgtccaag gagttgcctc gatggtctgc   761
ttctacggag ttcctcttct gattgtcaac gggttcttag ttttgatcac ttacttgcag   821
cacacgcatc cttccctgcc tcactatgac tcgtctgagt gggattggtt gaggggagct   881
ttggccaccg ttgacagaga ctacggaatc ttgaacaagg tcttccacaa atcacggac    941
acgcacgtgg cgcatcacct gttctcgacc atgccgcatt atcacgcgat ggaagctacg   1001
aaggcgataa agccgatact gggagagtat tatcagttcg atgggacgcc ggtggttaag   1061
gcgatgtgga gggaggcgaa ggagtgtatc tatgtggaac cggacaggca aggtgagaag   1121
aaaggtgtgt tctggtacaa caataagtta tga                              1154
```

```
<210> SEQ ID NO 4
<211> LENGTH: 96
<212> TYPE: PRT
<213> ORGANISM: Brassica napus

<400> SEQUENCE: 4

Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Ile Thr Ser Leu Ser Ser Leu Thr Leu
65                  70                  75                  80

Ser Pro Thr Ser Pro Gly Leu Ser Thr Gly Pro Ala Arg Ala Ala Ser
                85                  90                  95
```

```
<210> SEQ ID NO 5
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 5 atg ggt gca ggt gga aga atg caa gtg tct cct ccc tcc aag aag tct    48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act    96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg   144
Val Gly Glu Leu Lys Lys Ala Ile Pro Pro His Cys Phe Lys Arg Ser
            35                  40                  45
```

```
atc cct cgc tct ttc tcc tac ctc atc tgg gac atc atc ata gcc tcc      192
Ile Pro Arg Ser Phe Ser Tyr Leu Ile Trp Asp Ile Ile Ile Ala Ser
50              55                  60 tgc ttc tac tac gtc gcc acc act tac ttc cct ctc ctc cct cac cct      240
Cys Phe Tyr Tyr Val Ala Thr Thr Tyr Phe Pro Leu Leu Pro His Pro
65              70                  75                  80 ctc tcc tac ttc gcc tgg cct ctc tac tgg gcc tgc caa ggg tgc gtc      288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc      336
Leu Thr Gly Val Trp Val Ile Ala His Glu Cys Gly His His Ala Phe
            100                 105                 110 agc gac tac cag tgg ctt gac gac acc gtc ggt ctc atc ttc cac tcc      384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac      432
Phe Leu Leu Val Pro Tyr Phe Ser Trp Lys Tyr Ser His Arg Arg His
130                 135                 140 cat tcc aac act ggc tcc ctc gag aga gac gaa gtg ttt gtc ccc aag      480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg      528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg      576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct      624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc      672
Cys His Phe His Pro Asn Ala Pro Ile Tyr Asn Asp Arg Glu Arg Leu
210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac      768
Phe Arg Tyr Ala Ala Ala Gln Gly Val Ala Ser Met Val Cys Phe Tyr
                245                 250                 255 gga gtc ccg ctt ctg att gtc aat ggt ttc ctc gtg ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
        275                 280                 285 gat tgg ttg agg gga gct ttg gct acc gtt gac aga gac tac gga atc      912
Asp Trp Leu Arg Gly Ala Leu Ala Thr Val Asp Arg Asp Tyr Gly Ile
290                 295                 300 ttg aac aag gtc ttc cac aat att acc gac acg cac gtg gcg cat cat      960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365
```

```
gac agg caa ggt gag aag aaa ggt gtg ttc tgg tac aac aat aag tta    1152
Asp Arg Gln Gly Glu Lys Lys Gly Val Phe Trp Tyr Asn Asn Lys Leu
    370             375                 380 tga                                                                1155
```

<210> SEQ ID NO 6
<211> LENGTH: 384
<212> TYPE: PRT
<213> ORGANISM: Brassica napus

<400> SEQUENCE: 6

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350
```

```
Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
        370                 375                 380

<210> SEQ ID NO 7
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 7 atg ggt gca ggt gga aga atg caa gtg tct cct ccc tcc aag aag tct        48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act        96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg       144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc       192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct       240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc caa ggg tgc gtc       288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc       336
Leu Thr Gly Val Trp Val Ile Ala His Glu Cys Gly His His Ala Phe
            100                 105                 110 agc gac tac cag tgg ttt gac gac acc gtc ggt ctc atc ttc cac tcc       384
Ser Asp Tyr Gln Trp Phe Asp Asp Thr Val Gly Leu Ile Phe His Ser
        115                 120                 125 ttc ctc ctc gtc cct tac ttc tcc tgg aag tac agt cat cga cgc cac       432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag       480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg       528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg       576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct       624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc       672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc       720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac       768
Phe Arg Tyr Ala Ala Ala Gln Gly Val Ala Ser Met Val Cys Phe Tyr
```

```
                    245                 250                 255
gga gtc ccg ctt ctg att gtc aat ggt ttc ctc gtg ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
            275                 280                 285 gat tgg ttg agg gga gct ttg gct acc gtt gac aga gac tac gga atc      912
Asp Trp Leu Arg Gly Ala Leu Ala Thr Val Asp Arg Asp Tyr Gly Ile
    290                 295                 300 ttg aac aag gtc ttc cac aat att acc gac acg cac gtg gcg cat cat      960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
    370                 375                 380 tga                                                                  1155

<210> SEQ ID NO 8
<211> LENGTH: 384
<212> TYPE: PRT
<213> ORGANISM: Brassica napus

<400> SEQUENCE: 8

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Phe Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190
```

```
Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Gln Gly Val Ala Ser Met Val Cys Phe Tyr
            245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
        290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
        370                 375                 380

<210> SEQ ID NO 9
<211> LENGTH: 2601
<212> TYPE: DNA
<213> ORGANISM: Brassica napus

<400> SEQUENCE: 9
agagagagaa gagaggagac agagagagag tttgaggagg agcttcttcg tagggttcat      60
cgttattaac gttaaatctt catcccccc tacgtcagcc agctcaaggt cccttctttc     120
ttccatttct tctcatttta cgttgttttc aatcttggtc tgttctttc ttatcgcttt     180 tctgttctat ctatcatttt tgcatttcag tcgatttaat tctagatctg ttaatattta     240
ttgcattaaa ctatagatct ggtcttgatt ctctgttttc atgtgtgaaa tcttgatgct     300
gtctttacca ttaatctgat tatattgtct ataccgtgga gaatatgaaa tgttgcattt     360
tcatttgtcc gaatacaaac tgtttgactt tcaatctttt ttaatgattt attttgatgg     420
gttggtggag ttgaaaaatc accatagcag tctcacgtcc tggtcttaga aatatccttc     480
ctattcaaag ttatatatat ttgtttactt gtcttagatc tggacctgag acatgtaagt     540
acctatttgt tgaatctttg ggtaaaaaac ttatgtctct gggtaaaatt tgcttggaga     600
tttgaccgat tcctattggc tcttgattct gtagttacct aatacatgaa aaagtttcat     660
ttggcctatg ctcacttcat gcttacaaac ttttctttgc aaattaattg gattagatgc     720
tccttcatag attcagatgc aatagatttg catgaagaaa ataataggat tcatgacagt     780
aaaaaagatt gtattttgt ttgtttgttt atgtttaaaa gtctatatgt tgacaataga     840
gttgctctca actgtttcat ttagcttttt gttttgtca agttgcttat cttagagac     900 attgtgatta tgacttgtct tctctaacgt agtttagtaa taaagacga agaaattga     960 tatccacaag aaagagatgt aagctgtaac gtatcaaatc tcattaataa ctagtagtat    1020
tctcaacgct atcgtttatt tctttctttg gtttgccact atatgccgct tctctgctct    1080
```

-continued

| | |
|---|---|
| ttatcccacg tactatccat ttttttttgtg gtagtccatt tttttgaaac tttaataacg | 1140 |
| taacactgaa tattaatttg ttggtttaat taacttgag tctttgcttt tggtttatgc | 1200 |
| agaaacatgg gtgcaggtgg aagaatgcaa gtgtctcctc cctccaaaaa gtctgaaacc | 1260 |
| gacaacatca agcgcgtacc ctgcgagaca ccgcccttca ctgtcggaga actcaagaaa | 1320 |
| gcaatcccac cgcactgttt caaacgctcg atccctcgct cttctcccta cctcatctgg | 1380 |
| gacatcatca tagcctcctg cttctactac gtcgccacca cttactttccc tctcctccct | 1440 |
| caccctctct cctacttcgc ctggcctctc tactgggcct gccagggctg cgtcctaacc | 1500 |
| ggcgtctggg tcatagccca cgagtgcggc caccacgcct tcagcgacta ccagtggctg | 1560 |
| gacgacaccg tcggcctcat cttccactcc ttcctcctcg tcccttactt ctcctggaag | 1620 |
| tacagtcatc gacgccacca ttccaacact ggctccctcg agagagacga agtgtttgtc | 1680 |
| cccaagaaga agtcagacat caagtggtac ggcaagtacc tcaacaaccc tttgggacgc | 1740 |
| accgtgatgt taacggttca gttcactctc ggctggcctt tgtacttagc cttcaacgtc | 1800 |
| tcggggagac cttacgacgg cggcttcgct tgccatttcc accccaacgc tcccatctac | 1860 |
| aacgaccgtg agcgtctcca gatatacatc tccgacgctg gcatcctcgc cgtctgctac | 1920 |
| ggtctctacc gctacgctgc tgtccaagga gttgcctcga tggtctgctt ctacggagtt | 1980 |
| cctcttctga ttgtcaacgg gttcttagtt ttgatcactt acttgcagca cacgcatcct | 2040 |
| tccctgcctc actatgactc gtctgagtgg gattggttga ggggagcttt ggccaccgtt | 2100 |
| gacagagact acggaatctt gaacaaggtc ttccacaata tcacggacac gcacgtggcg | 2160 |
| catcacctgt tctcgaccat gccgcattat cacgcgatgg aagctacgaa ggcgataaag | 2220 |
| ccgatactgg gagagtatta tcagttcgat gggacgccgg tggttaaggc gatgtggagg | 2280 |
| gaggcgaagg agtgtatcta tgtggaaccg gacaggcaag gtgagaagaa aggtgtgttc | 2340 |
| tggtacaaca ataagttatg aagcaaagaa gaaactgaac cttctcttc tatgattgtc | 2400 |
| tttgtttaag aagctatgtt tctgtttcaa taatcttaat tatccatttt gttgtgttttt | 2460 |
| ctgacatttt ggctaaaatt atgtgatgtt ggaagttagt gtctaaaatg tcttgtgtct | 2520 |
| gtattgttct tcttctcatc gctgttatgt ttgggatcgt tgaaatgtga ctttcggact | 2580 |
| agtgaatctt gttctcgaac t | 2601 |

<210> SEQ ID NO 10
<211> LENGTH: 2666
<212> TYPE: DNA
<213> ORGANISM: Brassica napus

<400> SEQUENCE: 10

| | |
|---|---|
| gagaagagag agagagagag agagagagag agtgagtttg aggaggagct tcttcgtagg | 60 |
| gttcatcgtt attaacgtta aatcttcacc ccctacgtca gccagctcaa ggtccctttc | 120 |
| ttcttccatt tctttcatt ctacgttgtt ttcaatctta tgaaactttc tggtctgtgc | 180 |
| ttttcttatc gcttttctat tctatctatc atttttgcat ttcagtcgat ttaattctag | 240 |
| atctgttaat attaaactat agatctgttc ttgattctct gttttcatgt gtgaaatctg | 300 |
| atgctgtatt aatctgatta tattgtctat accgtggaga atatcaaatg ttgcattttc | 360 |
| atttgtccga atacaaagtg tttgactttc aatcgttttt aattatatat atatatatat | 420 |
| tttttgatgg gttggtggag ttgaaaaatc accatagcag tctcacgtcc tggttttaga | 480 |
| aatatcctat tcaaaattat atatttgttt acttgtttta gatctggacc tgagacatat | 540 |
| aagtacctat tgttgaatc tttgggtaaa aacttatgtc tctgggtaaa atttgctggg | 600 |

```
agatttgacc gattcctatt ggctcttgat tctgtagtta cgtaatacat gaaaaagttt    660
catttggcct atgctcactt catgcttata aacgttttct tgcaaattaa ttggattaga    720
tgttatttca tagattcagt cattcagata caatggagtt gcatgaagaa aataatagaa    780
ttcgtgacag taaaaagat tgtatttttg tttgtttgtt tatgtttaaa agtctatatg     840
ttgacaatag agttgctctc aactgtttca tttagcttct ttttttgtca agttgcttat    900
tcttagagac attgtgatta tgacttgtct tctttaacgt agtttagtaa taaaagacga    960
aagaaattga tatccacaag aaagagatgt gagctgtagc gtatcaaatc tcgttcattt   1020
actagtagta ttctcaacgc tatcgtttat ttatttttct ttcgttggtt tgccactata   1080
tgccacttct ctcctctttg tcccacgtac tatccatttt ttttgtggta gtccattttc   1140
ttgtaactta taataacgta actctgaatc ttttgtctgt agattaattt gttggtttaa   1200
ttaacttta agtctttgct tttggcttat gcagaaacat gggtgcaggt ggaagaatgc    1260
aagtgtctcc tccctccaag aagtctgaaa ccgacaccat caagcgcgta ccctgcgaga   1320
caccgccctt cactgtcgga gaactcaaga aagcaatccc accgcactgt ttcaaacgct   1380
cgatccctcg ctcttctcc tacctcatct gggacatcat catagcctcc tgcttctact    1440
acgtcgccac cacttacttc cctctcctcc ctcaccctct ctcctacttc gcctggcctc   1500
tctactgggc ctgccaaggg tgcgtcctaa ccggcgtctg ggtcatagcc cacgagtgcg   1560
gccaccacgc cttcagcgac taccagtggc ttgacgacac cgtcggtctc atcttccact   1620
ccttcctcct cgtcccttac ttctcctgga agtacagtca tcgacgccac cattccaaca   1680
ctggctccct cgagagagac gaagtgtttg tccccaagaa gaagtcagac atcaagtggt   1740
acggcaagta cctcaacaac cctttgggac gcaccgtgat gttaacggtt cagttcactc   1800
tcggctggcc gttgtactta gccttcaacg tctcgggaag accttacgac ggcggcttcg   1860
cttgccattt ccaccccaac gctcccatct acaacgaccg cgagcgtctc cagatataca   1920
tctccgacgc tggcatcctc gccgtctgct acggtctctt ccgttacgcc gccgcgcagg   1980
gagtggcctc gatggtctgc ttctacggag tcccgcttct gattgtcaat ggtttcctcg   2040
tgttgatcac ttacttgcag cacacgcatc cttccctgcc tcactacgat tcgtccgagt   2100
gggattggtt gaggggagct ttggctaccg ttgacagaga ctacggaatc ttgaacaagg   2160
tcttccacaa tattaccgac acgcacgtgg cgcatcatct gttctccacg atgccgcatt   2220
atcacgcgat ggaagctacc aaggcgataa agccgatact gggagagtat tatcagttcg   2280
atgggacgcc ggtggttaag gcgatgtgga gggaggcgaa ggagtgtatc tatgtggaac   2340
cggacaggca aggtgagaag aaaggtgtgt tctggtacaa caataagtta tgaggatatg   2400
atgatggtga agaacaaag aagatattgt cacgaacctt tctcttgctg tctctggtcg    2460
tctttgtttt aagaagctat gttttcgttt caataatctt aactatccat tttgttgtgt   2520
tttctgacat tttggctaaa attatgtgat gttggaagtt agtgtctaaa atgtcttgtg   2580
tctgtattgt tcttcttctc atcgctgtta tgtttgggat cgttgaaatg tgactttcgg   2640
actagtgaac tcttggttct cgaact                                        2666
```

<210> SEQ ID NO 11
<211> LENGTH: 1561
<212> TYPE: DNA
<213> ORGANISM: Brassica napus

<400> SEQUENCE: 11

```
gagaaccaga gagattcatt accaaagaga tagagagaga gagaaagaga ggagacagag     60
```

-continued

```
agagagtttg aggaggagct tcttcgtagg gttcatcgtt attaacgtta aatcttcatc    120
ccccccctacg tcagccagct caagaaacat gggtgcaggt ggaagaatgc aagtgtctcc   180
tccctccaaa aagtctgaaa ccgacaacat caagcgcgta ccctgcgaga caccgccctt   240
cactgtcgga gaactcaaga aagcaatccc accgcactgt ttcaaacgct cgatccctcg   300
ctctttctcc tacctcatct gggacatcat catagcctcc tgcttctact acgtcgccac   360
cacttacttc cctctcctcc ctcaccctct ctcctacttc gcctggcctc tctactgggc   420
ctgccagggc tgcgtcctaa ccggcgtctg ggtcatagcc cacgagtgcg gccaccacgc   480
cttcagcgac taccagtggc tggacgacac cgtcggcctc atcttccact ccttcctcct   540
cgtcccttac ttctcctgga agtacagtca tcgacgccac cattccaaca ctggctccct   600
cgagagagac gaagtgtttg tccccaagaa gaagtcagac atcaagtggt acggcaagta   660
cctcaacaac cctttgggac gcaccgtgat gttaacggtt cagttcactc tcggctggcc   720
tttgtactta gccttcaacg tctcggggag accttacgac ggcggcttcg cttgccattt   780
ccaccccaac gctcccatct acaacgaccg tgagcgtctc cagatataca ctctccgacgc  840
tggcatcctc gccgtctgct acggtctcta ccgctacgct gctgtccaag agttgcctc   900
gatggtctgc ttctacggag ttcctcttct gattgtcaac gggttcttag ttttgatcac   960
ttacttgcag cacacgcatc cttccctgcc tcactatgac tcgtctgagt gggattggtt  1020
gaggggagct ttggccaccg ttgacagaga ctacggaatc ttgaacaagg tcttccacaa  1080
tatcacggac acgcacgtgg cgcatcacct gttctcgacc atgccgcatt atcatgcgat  1140
ggaagctacg aaggcgataa agccgatact gggagagtat tatcagttcg atgggacgcc  1200
ggtggttaag gcgatgtgga gggaggcgaa ggagtgtatc tatgtggaac cggacaggca  1260
aggtgagaag aaaggtgtgt tctggtacaa caataagtta tgaagcaaag aagaaactga  1320
acctttctcw tcctatgatt gtctttgttt aagaagctat gtttctgttt caataatctt  1380
taattatcca ttttgttgtg ttttctgaca ttttggctaa aattatgtga tgttggaagt  1440
tagtgtctaa aatgtcttgt gtctgtattg ttcttcttct catcgctgtt atgtttggga  1500
tcgttgaaat gtgactttcg gactagtgaa ctcttgttct cgaactaaaa aaaaaaaaaa  1560
a                                                                  1561
```

<210> SEQ ID NO 12
<211> LENGTH: 1553
<212> TYPE: DNA
<213> ORGANISM: Brassica napus

<400> SEQUENCE: 12

```
gagacagatt cattaccaaa gagatagaga aagagagaga gagagagaga gagagagagt    60
gagtttgagg aggagcttct tcgtagggtt catcgttatt aacgttaaat cttcaccccc   120
tacgtcagcc agctcaagaa acatgggtgc aggtggaaga atgcaagtgt ctcctccctc   180
caagaagtct gaaaccgaca ccatcaagcg cgtaccctgc gagacaccgc cttcactgt   240
cggagaactc aagaaagcaa tcccaccgca ctgtttcaaa cgctcgatcc ctcgctcttt   300
ctcctacctc atctgggaca tcatcatagc ctcctgcttc tactacgtcg ccaccactta   360
cttccctctc ctccctcacc ctctctccta cttcgcctgg cctctctact gggcctgcca   420
agggtgcgtc ctaaccggcg tctgggtcat agcccacgag tgcggccacc acgccttcag   480
cgactaccag tggcttgacg acaccgtcgg tctcatcttc cactccttcc tcctcgtccc   540
ttacttctcc tggaagtaca gtcatcgacg ccaccattcc aacactggct ccctcgagag   600
```

```
agacgaagtg tttgtcccca agaagaagtc agacatcaag tggtacggca agtacctcaa      660
caacccttg  ggacgcaccg tgatgttaac ggttcagttc actctcggct ggccgttgta      720
cttagccttc aacgtctcgg gaagaccta  cgacggcggc ttcgcttgcc atttccaccc      780
caacgctccc atctacaacg accgcgagcg tctccagata tacatctccg acgctggcat      840
cctcgccgtc tgctacggtc tcttccgtta cgccgccgss cagggagtgg cctcgatggt      900
ctgcttctac ggagtcccgc ttctgattgt caatggtttc ctcgtgttga tcacttactt      960
gcagcacacg catccttccc tgcctcacta cgattcgtcc gagtgggatt ggttsagggg     1020
agctttggct accgttgaca gagactacgg aatcttgaac aaggtcttcc acaatattac     1080
cgacacgcac gtggcscatc atcygttctc cacgatgccg cattatcacg cgatggaagc     1140
taccaaggcg ataaagccga tactgggaga gtattatcag ttcgatggga cgccggtggt     1200
taaggcgatg tggagggagg cgaaggagtg tatctatgtg gaaccggaca ggcaaggtga     1260
gaagaaaggt gtgttctggt acaacaataa gttatgagga trraagaaac tgaacctttc     1320
tcttcctatg attgtctttg tttaagaagc tatgtttctg tttcaataat cttaattatc     1380
cattttgttg tgttttctga cattttggct aaaattatgt gatgttggaa gttagtgtct     1440
aaaatgtctt gtgtctgtat tgttcttctt ctcatcgctg ttatgtttgg gatcgttgaa     1500
atgtgactt  cggactagtg aactcttgtt ctcgaactaa aaaaaaaaaa aaa            1553
```

FAD-2 MUTANTS AND HIGH OLEIC PLANTS

FIELD OF THE INVENTION

The present invention relates to plants, seeds and products derived thereof, in particular to *Brassica* plants, seeds products derived thereof, that have mutant sequences conferring high oleic acid profile to the seed oil.

More particularly, the invention relates to mutant delta-12 fatty acid desaturase sequences, also referred to herein as mutant FAD2 sequences, in such plants which confer high oleic acid profile on the seed oil.

BACKGROUND

Delta-12 fatty acid desaturase (also known as oleic desaturase or oleate desaturase) is involved in the enzymatic conversion of oleic acid to linoleic acid.

Varieties with high level of oleic acid (possibly combined with low level of linolenic acid) are sought for many different applications (food applications, health applications, biodiesel applications and many others).

Mutant seeds providing an oil exhibiting a high oleic acid content (oleic acid content higher that 70 wt. % based upon the total weight of fatty acids present in the oil) previously reported in the literature had very poor agronomic value and/or bad root characteristics, and/or very low yield capacity.

There is still a need for material having stable, high oleic acid content (possibly combined with stable low linolenic acid content) across locations and across years, with also good agronomic performances and with normal oilseed rape morphology. In particular, the plants should have no fasciation and should have normal root development.

SUMMARY OF THE INVENTION

The present invention relates to a plant or a plant part or a seed containing a first FAD2 gene and possibly a second FAD2 gene, said first or said second FAD2 gene having a deletion at or corresponding to position 1421 (also referred to as DEL.1421) relative to a wild-type FAD2 gene, such as wild-type FAD2 gene of SEQ ID NO 9.

Another object of the present invention is a plant or a plant part or a seed containing a first FAD2 gene having a deletion at or corresponding to position 1421 relative to a wild-type FAD2 gene, such as wild-type FAD2 gene of SEQ ID NO 9, and a second FAD2 gene encoding a FAD-2 protein having an amino acid substitution at or corresponding to position 118 relative to a wild-type FAD-2 protein, such as the wild-type PAD-2 protein of SEQ ID NO 2 or 6.

A plant or a plant part or a seed of the invention preferably contains a nucleic acid sequence corresponding to SEQ ID NO 1 or 5, wherein the nucleotide (C) at position 215 is deleted, or contains a (variant) nucleic acid sequence, of at least 80%, preferably at least 85%, more preferably at least 90% and even more preferably at least 95%, 96%, 97%, 98% or 99% identity with SEQ ID NO 1 or 5, wherein the nucleotide corresponding to position 215 is deleted.

A plant or a plant part or a seed according to the invention can contain a (variant) nucleic acid sequence of at least 80%, preferably at least 85%, more preferably at least 90% and even more preferably at least 95%, 96%, 97%, 98% or 99% identity with SEQ ID NO 9, wherein the nucleotide corresponding to position 1421 is deleted (i.e. further deleted of the nucleotide corresponding to position 1421). Preferably, a plant or a plant part or a seed according to the invention contains a nucleic acid sequence corresponding to SEQ ID NO 9, wherein the nucleotide at position 1421 is deleted (i.e. further deleted of the nucleotide corresponding to position 1421).

A plant or a plant part or a seed according to the invention can contain a (variant) nucleic acid sequence of at least 80%, preferably at least 85%, more preferably at least 90% and even more preferably at least 95%, 96%, 97%, 98% or 99% identity with SEQ ID NO 10, wherein the nucleotide corresponding to position 1453 is deleted (i.e. further deleted of the nucleotide corresponding to position 1453). Preferably, a plant or a plant part or a seed according to the invention contains a nucleic acid sequence corresponding to SEQ ID NO 10, wherein the nucleotide at position 1453 is deleted (i.e. further deleted of the nucleotide corresponding to position 1453).

A preferred plant or a plant part or a seed according to the invention, further contains a nucleic acid sequence encoding a FAD-2 protein having an amino acid substitution at or corresponding to position 118 relative to a wild-type FAD-2 protein, such as the wild-type FAD-2 protein of SEQ ID NO 2 or 6. Preferably, said substituted amino acid at or corresponding to position 118 is phenylalanine.

A plant or a plant part or a seed according to the invention can be obtained by a mutagenesis treatment, more particularly by an Ethyl Methane Sulfonate (EMS) treatment.

Another object of the present invention is an isolated nucleic acid molecule comprising (or consisting of) the nucleic acid sequence of SEQ ID NO 1 or 5 wherein the nucleotide at position 215 is deleted (i.e. SEQ ID NO 1 or 5 further deleted of the nucleotide corresponding to position 215).

Also object of the invention is a (variant) nucleic acid molecule encoding a FAD2 protein (or a fragment of said protein), of at least 80%, preferably at least 85%, more preferably at least 90% and even more preferably at least 95%, 96%, 97%, 98% or 99% identity with SEQ ID NO 1 or 5, wherein the nucleotide corresponding to position 215 is deleted (i.e. further deleted of the nucleotide corresponding to position 215).

An isolated nucleic acid molecule according to the invention can comprise (or consist of) a (variant) nucleic acid sequence encoding a FAD2 protein (or a fragment), of at least 80%, preferably at least 85%, more preferably at least 90% and even more preferably at least 95%, 96%, 97%, 98% or 99% identity with SEQ ID NO 9, wherein the nucleotide corresponding to position 1421 is deleted (i.e. further deleted of the nucleotide corresponding to position 1421). Preferably, a nucleic acid molecule according to the invention comprises (or consists of) a nucleic acid sequence of SEQ ID NO 9, wherein the nucleotide at position 1421 is deleted (i.e. of SEQ ID NO 9 further deleted of the nucleotide corresponding to position 1421).

An isolated nucleic acid molecule according to the invention can comprise (or consist of) a (variant) nucleic acid sequence encoding a FAD2 protein (or a fragment), of at least 80%, preferably at least 85%, more preferably at least 90% and even more preferably at least 95%, 96%, 97%, 98% or 99% identity with SEQ ID NO 10, wherein the nucleotide corresponding to position 1453 is deleted (i.e. further deleted of the nucleotide corresponding to position 1453). Preferably, a nucleic acid molecule according to the invention comprises (or consists of) a nucleic acid sequence of SEQ ID NO 10, wherein the nucleotide at position 1453 is deleted (i.e. of SEQ ID NO 10 further deleted of the nucleotide corresponding to position 1453).

A preferred nucleic acid molecule of the invention comprises (or consists of) a nucleic acid sequence of SEQ ID NO 3, its complementary form or the RNA forms thereof.

Also object of the invention is a fragment of at least 10 nucleotides, preferably of at least 15, 20, 25, or 40 nucleotides, more preferably of at least 50 or 100 nucleotides of an isolated nucleic acid molecule of the invention, said fragment comprising the mutated codon resulting from said deletion.

Another object of the invention is a method of producing high oleic plant lines comprising:
a) inducing mutagenesis, preferably by means of EMS treatment, in at least some cells from a plant, more particularly of a *Brassica* plant, and preferably of a *Brassica napus* variety that has a oleic acid content of less than 70%;
b) regenerating plants from at least one of said mutagenized cells;
c) selecting regenerated plants which have a nucleic acid sequence according to the invention, and
d) deriving further generations of plants from said regenerated plants.

Said regenerated plants comprise a nucleic acid sequence of at least 80%, preferably at least 85%, more preferably at least 906 and even more preferably at least 95%, 96%, 97%, 98% or 99% identity with SEQ ID NO 9, wherein the nucleotide corresponding to position 1421 is deleted (i.e. further deleted of the nucleotide corresponding to position 1421), or a nucleic acid sequence of at least 80%, preferably at least 85%, more preferably at least 90% and even more preferably at least 95%, 96%, 97%, 98% or 99% identity with SEQ ID NO 10, wherein the nucleotide corresponding to position 1453 is deleted (i.e. further deleted of the nucleotide corresponding to position 1453).

Preferably, said regenerated plants comprise a nucleic acid sequence of SEQ ID NO 9 wherein the nucleotide 1421 is deleted (i.e. of SEQ ID NO 9 further deleted of the nucleotide corresponding to position 1421), or a nucleic acid sequence of SEQ ID NO 10 wherein the nucleotide 1453 is deleted (i.e. of SEQ ID NO 10 further deleted of the nucleotide corresponding to position 1453), or a nucleic acid sequence of SEQ ID NO 3.

More preferably, said regenerated plants further comprise a nucleic acid sequence encoding a FAD-2 protein having an amino acid substitution at or corresponding to position 118 relative to a wild-type FAD-2 protein, such as the wild-type FAD-2 protein of SEQ ID NO 2 or 6. Preferably, said substituted amino acid at or corresponding to position 118 is phenylalanine.

Step c) can comprise any method known in the art for identifying said mutation(s) (DEL.1421, DEL.1453, DEL.215 and possibly SNP1590), in particular step c) can comprise the use of restriction fragment length polymorphism (RFLP), random amplification polymorphism detection (RAPD), or polymerase chain reaction (PCR) method.

Another object is a method of producing high oleic plant lines comprising:
i. crossing a first plant of the invention with a second plant,
ii. obtaining seeds from the cross of step (a),
iii. growing fertile plants from such seeds,
iv. obtaining progeny seeds from the plants of step (c), and
v. identifying those seeds among the progeny that have high oleic acid content.

Step (v) of identifying said seeds can comprise the use of a nucleic acid molecule according to the invention.

More particularly, step (v) can comprise any method known in the art for identifying said mutation(s) according to the invention, and more particularly, step (v) can comprise the use of restriction fragment length polymorphism (RFLP), random amplification polymorphism detection (RAPD), or polymerase chain reaction (PCR) method.

Another object relates to a vegetable oil obtained from the seeds of the invention, said oil comprising more than (about) 72%, 75%, 80%, or 85% of oleic acid based upon the total weight of the fatty acids present in said oil.

Preferably, a vegetable oil according to the invention further comprises less than (about) 4%, 3.5%, 3%, 2%, 1% or 0.5% of linolenic acid.

BRIEF DESCRIPTION OF THE FIGURE

FIGS. 1A-1E correspond to the list of sequences of the present invention.

FIG. 2*a* shows the notification of acceptance for the deposit of the MSP05 variety.

FIG. 2*b* shows the first page of the viability statement for the MSP05 variety.

FIG. 2*c* shows the second page of the viability statement for the MSP05 variety.

FIG. 2*d* shows the notification of acceptance for the deposit of the 28DHS.086 variety.

FIG. 2*e* shows the first page of the viability statement for the 28DHS.086 variety.

FIG. 2*f* shows the second page of the viability statement for the 28DHS.086 variety.

FIG. 2*h* shows the first page of the viability statement for the MSP12 variety.

FIG. 2*i* shows the second page of the viability statement for the MSP12 variety.

DETAILED DESCRIPTION OF THE INVENTION

Figure 2G:
FIG. 2*g* shows the notification of acceptance for the deposit of the MSP12 variety.

The present invention relates to plants, more particularly to *Brassica* plants, preferably to *Brassica napus* varieties, which provide an oil having a oleic acid content higher than 70 wt. %, based upon the total weight of fatty acids present in the oil.

More particularly, a plant of the invention has at least one mutated FAD2 gene according to the invention.

Preferably, said mutated FAD2 gene confers high oleic acid content (i.e. a oleic acid content higher than 70 wt. %, based upon the total weight of fatty acids present in the oil) to seeds of said plants and to oil extracted from said seeds.

The present invention relates also to any part or any product of said plant bearing said at least one mutated FAD2 gene.

In the context of the present invention, a part or product of a plant is meant to encompass a leaf, cotyledon, stem, petiole, stalk, seed or any other tissue or fragment of tissue of said plant.

The present invention relates also to any progeny of said plant bearing said at least one mutated FAD2 gene of the invention.

In the context of the present invention, the term "progeny" refers to direct and indirect descendants, offspring and derivatives of a plant or plants of the invention and includes the first, second, third and/or subsequent generations, which may be produced by self crossing, crossing with plants with the same or different genotypes, and may be modified by range of suitable genetic engineering techniques.

The present invention also relates to said mutated FAD2 genes that confer high oleic acid content in seeds when present in a plant.

In particular, the invention relates to novel isolated nucleic acid molecules corresponding to novel variant forms of FAD2 genes having a deleted nucleotide at or corresponding to position 1421 relative to a wild type FAD2 gene, such as the wild type FAD2 gene represented by SEQ ID NO 9.

Said deletion alters the functionality of the resulting FAD2 gene product, whereby the level of oleic acid is increased, in plant expressing the mutant sequence(s), compared to the corresponding level in plant expressing the wild-type sequence(s).

In particular, a nucleic acid molecule of the invention can comprise (or consist of) a nucleotide sequence having at least 80%, preferably at least 85%, more preferably at least 90% and even more preferably at least 95%, 96%, 97%, 98% or 99% identity with any of SEQ ID NO 9, or with the complementary form or RNA form thereof, wherein the nucleotide at or corresponding to position 1421 is deleted (i.e. further deleted of the nucleotide corresponding to position 1421).

A nucleic acid molecule of the invention containing said deletion at or corresponding to position 1421 (also referred to as DEL.1421) can be derived from *Brassica napus* varieties, such as CONTACT, CABRIOLET, 28DHS.086 and/or MSP12 varieties.

The term "at position 1421" is to be understood as designating the nucleotide position 1421 in a wild-type FAD2 gene represented by SEQ ID NO 9, but also as referring to the nucleotide corresponding to said position in a wild-type or variant FAD2 gene that would have a different nucleic acid sequence due to deletions or additional nucleotides in the sequence.

The term "corresponding to position" as used herein means that a position is not only determined by the number of the preceding nucleotides. The position of a given nucleotide in accordance with the present invention may vary due to deletions or additional nucleotides in the nucleic acid sequence. Thus, under a "corresponding position" in accordance with the present invention it is to be understood that the nucleotide referred to may differ in the indicated number but still has similar neighbouring nucleotides in the linear sequence. For example, position 1453 in SEQ ID NO 10 or position 215 in SEQ ID NO 1 or 5 is such a position.

Similarly, the term "at position 118", is to be understood as designating the amino acid position 118 in a wild-type FAD2 protein represented by SEQ ID NO 2 or 6, but also as referring to the amino acid corresponding to said position in a wild-type or variant FAD2 protein that would have a different amino acid sequence due to deletions or additional amino acids in the polypeptide.

The term "corresponding to position" as used herein means that a position is not only determined by the number of the preceding amino acids. The position of a given amino acid in accordance with the present invention may vary due to deletions or additional amino acids in the polypeptide. Thus, under a "corresponding position" in accordance with the present invention it is to be understood that the amino acid(s) referred to may differ in the indicated number but still has (have) similar neighbouring amino acids in the linear sequence.

In another aspect, a nucleic acid molecule of the invention encodes a FAD2 protein having a substituted amino acid at or corresponding to position 118 relative to a wild type FAD2 protein, such as the wild type FAD2 protein represented by SEQ ID NO 2 or 6.

An isolated nucleic acid molecule of the invention contains at least one mutation, said mutation resulting in said substitution at or corresponding to position 118, preferably a substitution of tryptophan, more preferably a substitution of phenylalanine, for leucine, relative to a wild-type FAD2 protein, such as the wild-type FAD2 protein represented by SEQ ID NO 2 or 6.

Said mutation(s) alter(s) the functionality of the resulting FAD2 gene product, whereby the level of oleic acid is modified, preferably increased, in plant expressing the mutant sequence(s), compared to the corresponding level in plant expressing the wild-type sequence(s).

More particularly, a nucleic acid molecule of the invention encodes a FAD2 protein having a substitution of a phenylalanine for a leucine at position 118 relative to a wild type FAD2 protein represented by the amino acid sequence of SEQ ID NO 6.

A nucleic acid molecule of the invention can comprise (or consist of) a nucleic acid sequence of SEQ ID NO 1, 5, 9 or 10, wherein the codon encoding the amino acid at position 118 has at least one mutation to encode an amino acid different from leucine, and preferably to encode a phenylalanine at position 118 according to a FAD2 protein of the invention.

In other words, a nucleic acid molecule of the invention can comprise (or consist of) a nucleic acid sequence of SEQ ID NO 1, 5, 9 or 10, further comprising at least one mutation in the codon encoding the amino acid at position 118, to encode an amino acid different from leucine, and preferably to encode a phenylalanine at position 118.

A preferred nucleic acid molecule of the invention comprises (or consists of) a nucleic acid sequence of SEQ ID NO 7.

In another aspect, a nucleic acid molecule of the invention can encode a FAD2 protein having a deletion at position 118 relative to a wild type FAD2 protein, such as a wild type FAD2 protein represented by the amino acid sequence of SEQ ID NO 2 or 6.

More particularly, a nucleic acid molecule of the invention can encode a FAD2 protein having a leucine deleted at position 118 relative to a wild type FAD2 protein represented by the amino acid sequence of SEQ ID NO 2 or 6.

A nucleic acid molecule of the invention can comprise (or consist of) a nucleic acid sequence of SEQ ID NO 1, 5, 7, 9 or 10, wherein the codon encoding the amino acid at position 118 has been deleted (i.e. of SEQ ID NO 1, 5, 7, 9 or 10 further deleted of the codon encoding the amino acid at position 118).

It will be appreciated by the skilled person that the nucleic acid sequences of SEQ ID NO 1, 5, 7, 9 and 10 are not the only sequences that can be used to provide a FAD2 protein of the invention. Also contemplated are any nucleic acid molecules having different sequences but which, because of the degeneracy of the genetic code, encode a FAD2 protein comprising a substitution of an amino acid at position 118 (or corresponding to position 118) relative to the wild-type amino acid sequence, such as the wild-type FAD2 protein represented by SEQ ID NO 2 or 6.

In particular, a nucleic acid molecule of the invention can comprise (or consist of) a nucleotide sequence having at least 80%, preferably at least 85%, more preferably at least 90% and even more preferably at least 95%, 96%, 97%, 98% or 99% identity with any of SEQ ID NO 1, 5, 7, 9 and 10, or with the complementary form or RNA form thereof, encoding a FAD2 protein having an amino acid substitution at position 118 relative to a wild-type FAD2 protein.

A nucleic acid molecule of the invention having said mutation(s) resulting in said amino acid substitution at position 118 can be derived from *Brassica napus* varieties, such as 28DHS.086 variety and/or MSP12 variety.

More particularly, a nucleic acid molecule of the invention has a mutation at position 1590 (also referred to as SNP1590) of the acid nucleic sequence of SEQ ID NO 10, which causes a change in genetic codon from CTT to TTT, resulting in a substitution of an amino acid at position 118 relative to the wild-type amino acid sequence, such as the wild-type FAD2 protein represented by SEQ ID NO 6.

An isolated nucleic acid molecule of the invention containing said SNP1590 mutation, resulting in a substitution of phenylalanine for leucine at position 118, alters the functionality of the resulting FAD2 gene product, whereby the level of oleic acid is increased in plant expressing the mutant sequence, compared to the corresponding level in plant expressing the wild-type sequence.

In the framework of the invention, the term "SNP1590" refers to the single nucleotide polymorphism corresponding to said mutation at position 1590 of the nucleic acid of SEQ ID NO 10, and can refer also to the corresponding mutation in any nucleic acid molecule encoding a FAD2 protein of the invention having a substituted amino acid at position 118 (or corresponding to position 118) relative to the wild-type FAD2 protein, such as the wild-type FAD2 protein represented by SEQ ID NO 2 or 6.

Any fragment of a nucleic acid molecule of the invention of at least 10, 15, 20, 25, 50, 100 or more nucleotides and comprising at least one mutation resulting in a FAD2 protein according to the invention is contemplated.

In particular, a fragment of a nucleic acid molecule of the invention of at least 10, 15, 20, 25, 50, 100 or more nucleotides comprising said deletion DEL1421, DEL1453 or DEL215 or said SNP1590 is contemplated.

Also contemplated is a fragment of a nucleic acid molecule of the invention of at least 20, 25, 50, 100 or more nucleotides comprising said DEL1421 and said SNP1590.

Such fragments can be used as primers, as probes and/or as markers.

The nucleic acid fragments of the invention can be used as markers in plant genetic mapping.

In particular, the nucleic acid fragments of the invention can be used as markers in plant breeding programs.

Such markers may include restriction fragment length polymorphism (RFLP), random amplification polymorphism detection (RAPD), polymerase chain reaction (PCR) or self-sustained sequence replication (3SR) markers, for example.

Marker-assisted breeding techniques may be used to identify and follow a plant according to the invention or its progeny, also object of the invention, during the breeding process.

Marker-assisted breeding techniques may be used in addition to, or as an alternative to, other sorts of identification techniques.

An example of marker-assisted breeding is the use of PCR primers that specifically amplify a nucleic acid molecule of the invention.

The invention thereby provides methods for segregation and selection analysis of genetic crosses involving plants having nucleic acid sequences of the invention.

Also object of the present invention is a nucleic acid molecule of at least 10 or 15 nucleotides, preferably 20, 25, 50, 100 or more nucleotides, that hybridizes under stringent conditions to any nucleic acid sequence of SEQ ID NO 1, 3, 5, 7, and 9 to 12, which contains (or further contains) a mutation according to the invention.

An example of stringent hybridization conditions is hybridization at about 50° C., or at about 60° C. or higher, and 0.1×SSC (buffer of 0.15M NaCl, 0.015M trisodium citrate).

A method of the invention may for example involve determining the presence in a genome of particular FAD2 alleles containing at least said deletion at (or corresponding to) position 1421 relative to a wild type FAD2 gene, such as the wild type FAD2 gene represented by SEQ ID 9 and/or said substitution, SNP1590, (resulting in a substitution of phenylalanine for leucine) at (or corresponding to) position 118 relative to a wild type FAD2 protein, such as the wild type FAD2 protein represented by SEQ ID NO 2 or 6.

Such a determination may for example be achieved with a range of techniques, such as PCR amplification, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variant forms of that protein or from the wild-type.

More particularly, such fragments can be used in method of marker assisted selection for high oleic traits in plants, preferably in *Brassica* species, more particularly in *Brassica napus* varieties.

Another aspect of the present invention is related to a recombinant nucleotide sequence comprising, operably linked to a nucleotide sequence according to the invention, one or more adjacent regulatory sequence(s). Said adjacent regulatory sequence(s) is/are preferably originating from homologous organisms.

However said adjacent regulatory sequences may also be originating from heterologous organisms.

Said adjacent regulatory sequences are specific sequences such as promoters, enhancers, secretion signal sequences and/or terminators.

Another aspect of the invention is related to a vector comprising a nucleic acid molecule of the invention, possibly operably linked to one or more adjacent regulatory sequence(s) originating from homologous or from heterologous organisms.

In the present context "vector" is defined as any biochemical construct which may be used for the introduction of a nucleotide sequence (by transduction, transfection, transformation, infection, conjugation, etc.) into a cell.

Advantageously, a vector according to the invention is selected from the group consisting of plasmids (including replicative and integrative plasmids), viruses, phagemids, chromosomes, transposons, liposomes, cationic vesicles, or a mixture thereof. Said vector may already comprise one or more adjacent regulatory sequence(s), allowing the expression of said nucleic acid molecule and its transcription into a polypeptide of the invention.

The present invention also encompasses any peptide, which may still have a delta-12 oleate desaturase activity, resulting from the expression of a nucleic acid of the invention containing said deletion (DEL1421, DEL1453 or DEL215), such as the peptide of SEQ ID NO 4.

Nucleic acid molecules, recombinant nucleic acid molecules, and/or vectors of the present invention are useful to transform target plants, and thereby confer altered FAD2 gene product, whereby the level of oleic acid is modified, preferably increased, in plant expressing a mutant FAD2 of the invention, compared to the corresponding level in plant expressing the wild-type sequence.

The present invention is also related to a transformed host cell, or recombinant host cell, containing (or having incorporated) one or more of the nucleotide sequences and/or vectors according to the invention having the deletion 1421.

In the present context, a "transformed host cell" or "recombinant cell", also referred to as "transformant", is a cell having incorporated one or more of the nucleotide sequences and/or vectors according to the invention. The transformed host cell may be a cell in which said vector(s) and/or said nucleotide sequence(s) is/are introduced by means of genetic transformation, preferably by means of homologous recombination, or by any other well known methods used for obtaining a recombinant organism.

Any method by which the novel sequence can be incorporated into the host genome is contemplated by the present invention.

More particularly, any method by which the novel sequence can be incorporated into the host genome, and stably inherited by its progeny, is contemplated by the present invention.

A broad range of known techniques currently exist for achieving direct or indirect transformation of higher plants with exogenous DNA.

Transformation of plant cells can be mediated by the use of vectors. A common method of achieving transformation is the use of *Agrobacterium tumefaciens* to introduce a foreign gene into the target plant cell.

Plant viruses also provide a possible means for transfer of exogenous DNA.

Direct uptake of plant cells can also be employed. Typically, protoplasts of the target plant are placed in culture in the presence of the nucleic acid molecules to be transferred, and an agent which promotes the uptake of said nucleic acid molecules by protoplast. Useful agents in this regard are polyethylene glycol or calcium phosphate.

Alternatively, nucleic acid molecules uptake can be stimulated by electroporation. In this method, an electrical pulse is used to open temporary pores in a protoplast cell membrane, and said nucleic acid molecules in the surrounding solution are then drawn into the cell through the pores. Similarly, microinjection can be employed to deliver said nucleic acid molecules directly into a cell, and preferably directly into the nucleus of the cell.

In these techniques, transformation occurs in a plant cell in culture. Subsequent to the transformation event, plant cells can be regenerated to whole plants.

Techniques for the regeneration of mature plants from callus or protoplast culture are well known.

Alternate methods are also available which do not necessarily require the use of isolated cells, and therefore, plant regeneration techniques, to achieve transformation. These are generally referred to as "ballistic" or "particle acceleration" methods, in which nucleic acid molecules coated metal particles are propelled into plant cells by either a gunpowder charge or electrical discharge. In this manner, plant cells in culture or plant reproductive organs or cells, e.g. pollen, can be stably transformed with the nucleic acid molecules of interest.

The present invention can be applied to transformation of virtually any type of plant, monocotyledons or dicotyledons.

Suitable plants to be transformed are preferably oil producing crops, such as sunflower, soybean, cotton, corn, etc., preferably *Brassica* species, more preferably *Brassica napus* varieties.

The present invention relates to a plant or a plant part or a seed containing a first FAD2 gene and possibly a second FAD2 gene, said first or said second FAD2 gene having said deletion (DEL.1421, DEL.1453 or DEL.215).

More particularly, a plant or a plant part or a seed of the invention contains a first FAD2 gene and possibly a second FAD2 gene, said first or said second FAD2 gene having a deletion at or corresponding to position 1421 (also referred to as DEL.1421) relative to a wild-type FAD2 gene, such as wild-type FAD2 gene of SEQ ID NO 9.

Preferably, a plant or a plant part or a seed of the invention contains a first FAD2 gene having a deletion at or corresponding to position 1421 relative to a wild-type FAD2 gene, such as wild-type FAD2 gene of SEQ ID NO 9, and a second FAD2 gene encoding a FAD-2 protein having an amino acid substitution at or corresponding to position 118 relative to a wild-type FAD-2 protein, such as the wild-type FAD-2 protein of SEQ ID NO 2 or 6.

In particular, a plant or a plant part or a seed of the invention preferably contains a nucleic acid sequence corresponding to SEQ ID NO 1 or 5, wherein the nucleotide (C) at position 215 is deleted (i.e. corresponding to SEQ ID NO 1 or 5 further deleted of the nucleotide at position 215), or contains a (variant) nucleic acid sequence, of at least 80%, preferably at least 85%, more preferably at least 90% and even more preferably at least 95%, 96%, 97%, 98% or 99% identity with SEQ ID NO 1 or 5, wherein the nucleotide corresponding to position 215 is deleted (i.e. with SEQ ID NO 1 or 5 further deleted of the nucleotide corresponding to position 215).

Examples of such plants are CONTACT and CABRIOLET varieties, which are registered varieties.

A preferred plant or a plant part or a seed according to the invention, further contains a nucleic acid sequence encoding a FAD-2 protein having an amino acid substitution at or corresponding to position 118 relative to a wild-type FAD-2 protein, such as the wild-type FAD-2 protein of SEQ ID NO 2 or 6. Preferably, said substituted amino acid at or corresponding to position 118 is phenylalanine.

Examples of such plants are 28DHS.086 and MSP12 varieties.

MSP05 variety is maintained as a Budapest Treaty patent deposit with NCIMB, 23 St. Machar Drive, Aberdeen, AB24 3RY, Scotland, under accession number NCIMB 41233 made Jul. 9, 2004.

28DHS.086 variety is maintained as a Budapest Treaty patent deposit with NCIMB, Bucksburn, Aberdeen, AB21 9YA, Scotland, under accession number NCIMB 41365 made Dec. 22, 2005.

MSP12 variety is maintained as a Budapest Treaty patent deposit with NCIMB, Bucksburn, Aberdeen, AB21 9YA, Scotland, under accession number NCIMB 41374 made Feb. 10, 2006.

A mutated plant or a plant part or a seed according to the invention exhibits the surprising advantage of developing a good rooting system. More particularly, having regard to a mutated *Brassica napus* variety according to the invention, the principal root and the secondary rooting system have a length comparable (similar) to respectively the principal root and the secondary rooting system of wild-type varieties. In comparison, mutated *Brassica* napus obtained by carrying out the method described in WO98/56239 shows a principal root much smaller than the wild-types and a secondary rooting system severely impaired.

A plant or a plant part or a seed according to the invention can be obtained by a mutagenesis treatment, more particularly by an Ethyl Methane Sulfonate (EMS) treatment.

Another object of the invention is a method of producing high oleic plant lines comprising: (a) crossing a first plant with a second plant having at least one FAD2 gene having said deletion according to the invention, (b) obtaining seeds from the cross of step (a), (c) growing fertile plants from such seeds; (d) obtaining progeny seeds from the plants of step (c), and (e) identifying those seeds among the progeny that have high oleic acid content.

In said method of producing high oleic plant lines, said second plant preferably have a second mutant FAD2 gene having said SNP1590 mutation.

In another aspect, the invention provides a method for increasing the oleic acid content of plants, more particularly of *Brassica* plants, and preferably of *Brassica napus* plants comprising the steps of:

(a) inducing mutagenesis in at least some cells from a plant, more particularly of a *Brassica* plant, and preferably of a *Brassica napus* plant that has a oleic acid content of less than 70%;
(b) regenerating plants from at least one of said mutagenized cells;
(c) selecting regenerated plants which have a nucleic acid sequence of the invention and/or which expresses a FAD2 protein of the invention; and
(d) deriving further generations of plants from said regenerated plants.

Preferably, the seeds obtained from said plants provide an oil having an oleic acid content of more than 70 wt. %, more preferably of more than 75 wt. %, based upon the total weight of fatty acid present the oil.

Another object of the invention is a vegetable oil obtained from at least one plant according to the invention, which vegetable oil comprises more than (about) 70%, 72%, 75%, 80%, or 85% of oleic acid.

More particularly, a vegetable oil of the invention, obtained preferably from at least one *Brassica* species of the invention, more preferably from at least one *Brassica napus* variety according to the invention, comprises more than (about) 70%, 72%, 75%, 80%, or 85% of oleic acid. Said oil can further comprise less than (about) 4%, 3.5%, 3%, 29%, 19% or 0.5% of linolenic acid, based upon the total weight of the fatty acids present in the oil.

Preferably, said oil comprises more than (about) 70%, 72%, 75%, 80%, 81%, 82%, 83%, 84%, 85%, 86%, 87%, 88%, 89% or 90%, preferably between (about) 70% and (about) 90%, more preferably between (about) 72% and (about) 89% of oleic acid. Said oil can further comprise less than (about) 4%, 3.5%, 3%, 2%, 1%, or 0.5%, preferably between (about) 4% and (about) 0.4% of linolenic acid, based upon the total weight of the fatty acids present in the oil.

According to a preferred embodiment, two double low winter rapeseed varieties (ENVOL and LIBERATOR) were submitted to an Ethyl Methane Sulfonate (EMS) treatment in 1992. The EMS treatment was performed at 2.5% and 5% for 4 h or 8 h.

The M1 generation was grown in a greenhouse after 8 weeks of vernalization in a growth chamber and then harvested in July 93.

M1 seeds were planted in the field in September 93, bagged at the beginning of flowering and M2 seeds harvested in July 94.

M2 seeds were planted in September 94, bagged at the beginning of flowering and M3 seeds harvested in July 95.

The progenies were then analysed for fatty acid composition using gas chromatography based analytical method, as commonly known in this area of technology.

All progenies showing an oleic content higher than 68% were kept.

Selected progeny was replanted in the field in September 1995, bagged in April then harvested in July 1996.

At this stage progenies were screened for good agronomic and morphological characteristics, such as good germination capacity, good autumn vigor, good winter hardiness, good rooting system, good blackleg and light leaf spot resistance as well as excellent lodging resistance.

Material which was too tall and too late was eliminated as well as material showing strong fasciation.

Analysis of the remaining progeny was again done by gas chromatography to select individuals with oleic acid levels higher than 68%. All of these individuals were planted in the field in September 1996-1997.

A progeny called MUT 152-96 looked particularly interesting in terms of agronomic and morphological characteristics, as well as for its oleic acid content. It was cultivated in isolation during the crop season of September 1.996-1997. The most interesting progenies in terms of agronomic and morphological characteristics were selected for bagging and crossing.

Crossing was performed with double low winter oilseed rape varieties having a conventional fatty acid profile (i.e. oleic acid below 70%) or with low linolenic acid content (i.e. less than about 3.5%) in order to develop lines with a high oleic acid content associated with low linolenic acid content (HOLL).

The material was progressed into pedigree breeding, self pollination until at least the F7 generation.

At all generations strong selection pressure was applied against fasciation and for normal plant development and normal rooting system.

Fatty acid composition was monitored in each generation and only material with oleic acid content higher than 75% and linolenic acid content below 3.5% was kept.

Different HOLL varieties were obtained by this process such as for example MSP05.

And by crossing MSP05 variety and CABRIOLET variety, 28DHS.086 variety was obtained.

MSP12 was developed by the same breeding process than MSP05 but as among starting parent CONTACT was used instead of parents having a conventional fatty acid profile.

The double low varieties with conventional fatty acid profiles used in this work were BRISTOL, CAPITOL, CAPVERT, VIVOL and CAIMAN and these varieties have been multiplied or maintained using the same maintenance scheme as described here above for the HOLL lines (in accordance with the technical rules published by the "GNIS" and edited by SEDIS, e.g. see 2003 edition, vol. 1, pp. 135-147 related to crop plants).

Basic seed was used for the determination of fatty acid content in trials—small research trials (6 to 12 m$^2$) or development trials (500 m$^2$) and for the sequencing work.

EXAMPLES

Example 1

The seeds were grinded in a first solution consisting of methanol (800 ml), trimethyl-pentane (200 ml) and 5 g of Na OH. About 3 ml of solution was used for about 10 g of seeds (in other words about 10 to 50 seeds for 1 ml of solution).

Extraction was performed during 20 minutes and thereafter a second solution, consisting of trimethylamine (900 ml), and propanol, 2-(100 ml), was added at the same volume as the first solution.

The resulting solution was vortexed and allowed to rest until formation of an upper phase.

The upper phase was sampled and transferred into viols.

One microliter of same was injected in a gas chromatograph (Fisons from thermo-electron with a column DB3-30 meter with a diameter of 0.25 mm and a thickness of 25 micrometer). Running time was about 4 min.

The oleic acid content results are summarized in table 1.

TABLE 1

| Varieties | Oleic acid content (wt. %) | Appreciation |
|---|---|---|
| CONTACT | 71.8-75.2 | High |
| CABRIOLET | 73.2-76.8 | High |

TABLE 1-continued

| Varieties | Oleic acid content (wt. %) | Appreciation |
|---|---|---|
| 28DHS086 | 80.3-83.1 | Very high |
| MSP12 | 80.3-83.5 | Very high |
| MSP05 | 78.1-81.9 | Very high |
| BRISTOL | 61.4-65.7 | Normal |
| VIVOL | 60.8-63.2 | Normal |
| CAPVERT | 58.9-65.9 | Normal |
| CAIMAN | 61.9-64.0 | Normal |
| CAPITOL | 59.7-64.6 | Normal |

The oleic acid content is based on the total weight of the fatty acid in the extracted oil.

Example 2

Plant materials used for sequencing are:
mutant lines with higher oleic fatty acid content: CONTACT, CABRIOLET and 28DHS.086; and
wild type varieties with normal oleic acid content: Bristol, Capitol, Vivol, Capvert and Caiman.

All these lines were grown in a growth chamber and the cotyledons and stems were collected from 7-day-old plants.

The plant tissues were freeze-dried and used for DNA extraction.

DNA was isolated with Qiagen Plant DNA kits (Qiagen INC.-USA, Valencia Calif.).

PCR was performed with TaqGold protocol (AB Biosystem, Inc,).

Reaction mix includes 2.5 µl 10× buffer, 0.2 µl TaqGold, 0.2 µl dNTP (25 mM), 2 µl primers (5 uM) and 10 ul DNA template (2 ng/ul) and 10.1 ul $H_2O$.

PCR cycles were as follows: 94° C. 5 min; 8 cycles of 94° C. 40 sec, 62° C. 40 sec, 72° C. 1 min, 94° C. 40 sec, 60° C. 40 sec, 72° C. 1 min, 94° C. 40 sec, 58° C. 40 sec, 72° C. 1 min, 94° C. 40 sec, 56° C. 40 sec, 72° C. 1 min; 3 cycles of 94° C. 40 sec, 55° C. 40 sec, 72° C. 1 min; hold at 72° C. for 7 min.

PCR products were analyzed on 1% agarose gel.

For sequencing, 5 µl PCR products were removed to a new tube and 1 µl ExonucleaseI (1:50 dilution) and 1 µl Shrimp Alkaline Phosphatase (1:5 dilution).

The mix was incubated at 37° C. for 20 min and then 80° C. for 15 min to inactivate the enzymes.

40 µl $H_2O$ was added and 6 µl were used as template with 1 µl sequencing primer.

Sequencing was done on 3730 DNA Analyzer (Applied Biosystems).

Sequences were assembled and aligned using SeqMan II program of the LaserGene (DNASTAR, INC, Madison. WI).

Example 3

Four *Brassica napus* delta-12 oleate desaturase (FAD2) gene sequences, 4684997, 46399190, 8705228 and 4092878, were downloaded from Genebank (NCBI). These sequences were used as queries to blast against Monsanto sequence database.

Using the "blastn" programs (NCBI), a number of high score hits were obtained. All the hit sequences were downloaded and reassembled with the SeqmanII program (DNASTAR Inc, Madison, Wis., USA).

Two distinct transcripts were identified and designated as Fad2-1 (SEQ ID NO 11) and Fad2-2 (SEQ ID NO 12). Fad2-1 and Fad2-2 share a high sequence homology, with 97% sequence identity.

To identify causative mutations associated with high oleic acid content in the mutant lines and their progenies, nested locus-specific primers were designed to cover the entire sequences.

The 3' end of a primer was always located at a nucleotide that differentiated Fad2-1 from Fad2-2 except those located at 5' and 3' ends of the consensus sequences where there was not differential nucleotide between the two genes.

The primers were also designed in such way that one amplicon would overlap with another to ensure full coverage of the entire sequence. These primers were arrayed and used to generate locus-specific amplicons on mutants and wild types. Sequencing results indicated that all the locus-specific PCR primers behaved as expected.

Sequences belonging to the same gene were assembled together using SeqManII program.

The consensus genomic sequences of the wild-type Fad2-l and Fad2-2 genes are represented respectively by SEQ ID NO 9 and 10.

Table 2 summarizes the sequence features of both Fad2-1 and Fad2-2 genes.

TABLE 2

| Features | FAD2-1 position | FAD2-2 position |
|---|---|---|
| Gene | 1-2601 | 1-2666 |
| 5' UTR | 1-1206 | 1-1238 |
| Exon | 1-108 | 1-111 |
| Intron | 109-1202 | 112-1234 |
| Exon | 1207-2601 | 1235-2619 |
| CDS | 1207-2361 | 1239-2393 |
| 3 'UTR | 2362-2601 | 2394-2666 |

The features are based on the consensus genomic sequences from multiple reads on different genotypes.

Both Fad2-1 and Fad2-2 genes have one intron each.

The intron sizes are slightly different between two genes. For Fad2-1, intron spans 1105 bp starting from position 109 to 1213, while for Fad2-2, intron consists of 1123 bp starting from position 112 to 1234 on the consensus sequences.

The intron is located at 5' UTR region.

Putative translation initiation codons are located at 1207 and 1239 for Fad2-1 and Fad2-2 genes, respectively.

The translation termination codons are located at 2370-2372 and 2391-2393, respectively for Fad2-1 and Fad2-2.

3' UTR sequences are 247 base pairs for Fad2-1 and 273 base pairs for Fad2-2 genes.

A deletion at position 1421 (called DEL.1421) of FAD2-1 gene caused a frame-shift in genetic codons, resulting in premature termination of the polypeptides.

A point mutation at position 1590 (SNP1590) of FAD2-2 gene (as represented by SEQ ID NO 7) caused an amino acid residue change from leucine (CTT) to phenylalanine (TTT).

Both leucine and phenylalanine are hydrophobic in nature and share some common amino acid properties, but phenylalanine contains a large rigid aromatic group on the side chain that causes some change in the function of the enzyme.

Moreover, in combination with DEL.215, this mutation causes more visible effect on the phenotype.

Combination of different alleles at these mutations created a gradient on oleic content as observed on different mutant lines (see table 1).

Two mutant lines, 28DHS.086 and MSP12, carried double mutations at DEL1421 and SNP1590. Since both mutations were missense mutations, the FAD2 gene functions are severely affected, resulting in the highest oleic content in the mutant line.

It is to be noted that *Brassica napus* varieties carrying only the SNP1590 mutation exhibits a normal oleic acid content (i.e. an oleic acid content equivalent to the oleic acid content of the wild-types).

Two mutant lines, CONTACT and CABRIOLET, carried a single point mutation at DEL.1421, resulting in an oleic content slightly below in comparison with the double mutants.

In summary, the sequence data strongly indicated that these mutations, at Fad2-1 and Fad2-2 are associated with oleic contents on different mutant lines.

The identification of causative sequence variations is crucial to design diagnostic assays specifically for each mutant allele.

Knowledge of association between sequence variations and phenotypes can allow to design marker assays to accurately predict the oleic acid content in plants without the need of wet chemical analysis of the fatty acid content.

---

The invention claimed is:

1. An isolated nucleic acid molecule encoding a FAD2 protein having reduced desaturase activity, wherein the molecule comprises a nucleotide sequence selected from the group consisting of:
    (a) the nucleotide sequence of SEQ ID NO: 1 wherein the nucleotide at position 215 is deleted;
    (b) the nucleotide sequence of SEQ ID NO: 5 wherein the nucleotide at position 215 is deleted;
    (c) the nucleotide sequence of SEQ ID NO: 3, its complementary form, or the RNA form thereof;
    (d) a nucleotide sequence having at least 95% identity with the nucleotide sequence of SEQ ID NO: 1 wherein the nucleotide corresponding to position 215 is deleted;
    (e) a nucleotide sequence having at least 95% identity with the nucleotide sequence of SEQ ID NO: 5 wherein the nucleotide corresponding to position 215 is deleted;
    (f) a nucleotide sequence fragment comprising at least 10 contiguous nucleotides of an isolated nucleic acid molecule of (a), wherein the fragment comprises a mutated codon resulting from the deletion at position 215; and
    (g) a nucleotide sequence fragment comprising at least 10 contiguous nucleotides of an isolated nucleic acid molecule of (b), wherein the fragment comprises a mutated codon resulting from the deletion at position 215.

2. The isolated nucleic acid molecule of claim 1, further comprising a nucleotide sequence selected from the group consisting of:
    (a) the nucleotide sequence of SEQ ID NO: 9 wherein the nucleotide at position 1421 is deleted;
    (b) a nucleotide sequence having at least 95% identity with the nucleotide sequence of SEQ ID NO: 9 wherein the nucleotide corresponding to position 1421 is deleted; and
    (c) a nucleotide sequence fragment comprising at least 10 contiguous nucleotides of an isolated nucleic acid molecule of (a), wherein the fragment comprises a mutated codon resulting from the deletion at position 1421.

3. An isolated nucleic acid molecule encoding a FAD2 protein having reduced desaturase activity, wherein the molecule comprises a nucleotide sequence selected from the group consisting of:
    (a) the nucleotide sequence of SEQ ID NO: 9 wherein the nucleotide at position 1421 is deleted;
    (b) the nucleotide sequence of SEQ ID NO: 10 wherein the nucleotide at position 1453 is deleted;
    (c) a nucleotide sequence having at least 95% identity with the nucleotide sequence of SEQ ID NO: 9 wherein the nucleotide corresponding to position 1421 is deleted;
    (d) a nucleotide sequence having at least 95% identity with the nucleotide sequence of SEQ ID NO: 10 wherein the nucleotide corresponding to position 1453 is deleted;
    (e) a nucleotide sequence fragment comprising at least 10 contiguous nucleotides of an isolated nucleic acid molecule of (a), wherein the fragment comprises a mutated codon resulting from said deletion; and
    (f) a nucleotide sequence fragment comprising at least 10 contiguous nucleotides of an isolated nucleic acid molecule of (b), wherein the fragment comprises a mutated codon resulting from said deletion.

4. A vector comprising a nucleic acid molecule according to claim 1.

5. A host cell comprising a nucleic acid molecule according to claim 1.

6. A plant stably transformed with a vector of claim 4.

7. A method of enhancing the oleic acid content in a plant comprising transforming a plant with the vector of claim 4.

8. A method of producing high oleic plant lines, the method comprising:
    (a) inducing mutagenesis in a cell from a plant that has an oleic acid content of less than 70%;
    (b) regenerating a plant from said mutagenized cell;
    (c) selecting regenerated plants which have a nucleic acid sequence according to claim 1; and
    (d) deriving further generations of plants from said regenerated plants.

9. The method according to claim 8, wherein the cell from a plant is from a *Brassica* plant.

10. The method according to claim 9, wherein the *Brassica* plant is a *Brassica napus* plant.

11. The method according to claim 8, wherein said regenerated plant further comprises a nucleic acid sequence encoding a FAD2 protein having an amino acid substitution at or corresponding to position 118 relative to a wild-type FAD2 protein of SEQ ID NO: 2 or SEQ ID NO: 6.

12. The method according to claim 8, wherein the mutagenesis is induced by ethyl methane sulfonate treatment.

13. A plant obtained by the method according to claim 8.

14. A method of producing high oleic plant lines, the method comprising:
    (a) crossing a first plant of claim 6 with a second plant,
    (b) obtaining seeds from the cross of step (a),
    (c) growing fertile plants from the seeds,
    (d) obtaining progeny seeds from the plants of step (c), and
    (e) identifying those seeds among the progeny that have high oleic acid content.

15. A method of producing high oleic plant lines, the method comprising:
    (a) crossing a first plant of claim 13 with a second plant,
    (b) obtaining seeds from the cross of step (a),
    (c) growing fertile plants from the seeds,
    (d) obtaining progeny seeds from the plants of step (c), and
    (e) identifying those seeds among the progeny that have high oleic acid content.

16. An assay kit comprising a first container containing a nucleic acid molecule of claim 1.

* * * * *